(12) United States Patent
Jarvius et al.

(10) Patent No.: US 10,829,797 B2
(45) Date of Patent: Nov. 10, 2020

(54) METHOD FOR DETERMINING ANTIMICROBIAL SUSCEPTIBILITY OF A MICROORGANISM

(71) Applicant: Q-LINEA AB, Uppsala (SE)

(72) Inventors: Jonas Jarvius, Uppsala (SE); Jan Grawe, Uppsala (SE); Ylva Molin, Uppsala (SE); Markus Klintstedt, Uppsala (SE); Mats Gullberg, Sollentuna (SE)

(73) Assignee: Q-linea AB, Uppsala (SE)

( * ) Notice: Subject to any disclaimer, the term of this patent is extended or adjusted under 35 U.S.C. 154(b) by 215 days.

(21) Appl. No.: 15/737,208

(22) PCT Filed: Jun. 16, 2016

(86) PCT No.: PCT/EP2016/063952
§ 371 (c)(1),
(2) Date: Dec. 15, 2017

(87) PCT Pub. No.: WO2016/207065
PCT Pub. Date: Dec. 29, 2016

(65) Prior Publication Data
US 2018/0223327 A1 Aug. 9, 2018

(30) Foreign Application Priority Data
Jun. 24, 2015 (GB) .................................. 1511129.7

(51) Int. Cl.
*C12Q 1/18* (2006.01)
*C12M 1/26* (2006.01)
*C12M 1/34* (2006.01)

(52) U.S. Cl.
CPC ............... *C12Q 1/18* (2013.01); *C12M 33/00* (2013.01); *C12M 41/30* (2013.01)

(58) Field of Classification Search
CPC ......... H01L 2924/0002; H01L 2924/00; H01L 2023/405; H01L 2023/4062; H01L 2023/4087; H01L 23/4006; H01L 23/427; C12M 33/00; C12M 41/30; C12Q 1/18
See application file for complete search history.

(56) References Cited

U.S. PATENT DOCUMENTS

| | | | |
|---|---|---|---|
| 4,132,599 A * | 1/1979 | Fletcher | C12Q 1/18 435/32 |
| 5,789,173 A | 8/1998 | Peck et al. | |
| 7,547,526 B2 | 6/2009 | Ladisch et al. | |
| 7,893,251 B2 | 2/2011 | Lorenz | |
| 8,460,887 B2 | 6/2013 | Goldberg et al. | |
| 8,481,265 B2 | 7/2013 | Peytavi et al. | |
| 8,652,800 B2 | 2/2014 | Walsh et al. | |
| 8,780,181 B2 | 7/2014 | Olesen et al. | |
| 2005/0095665 A1 | 5/2005 | Williams et al. | |
| 2005/0202487 A1 | 9/2005 | Klepp et al. | |
| 2010/0124763 A1 | 5/2010 | Walsh et al. | |
| 2010/0184210 A1 | 7/2010 | Rossmanith et al. | |
| 2011/0294128 A1 | 12/2011 | Peytavi et al. | |
| 2012/0231446 A1 | 9/2012 | Heckel et al. | |
| 2013/0052636 A1 * | 2/2013 | Verma | C12M 41/46 435/5 |
| 2013/0171615 A1 | 7/2013 | Van Meerbergen et al. | |
| 2014/0278136 A1 | 9/2014 | Shamsheyeva et al. | |

FOREIGN PATENT DOCUMENTS

| | | |
|---|---|---|
| EP | 0 976 821 A1 | 2/2000 |
| WO | WO 98/47999 A1 | 10/1998 |
| WO | WO 01/85664 A2 | 11/2001 |
| WO | WO 03/012119 A2 | 2/2003 |
| WO | WO 2011/086462 A1 | 7/2011 |
| WO | WO 2014/040088 A1 | 3/2014 |
| WO | WO 2015/189390 A1 | 12/2015 |
| WO | WO 2016/207065 A1 | 12/2016 |

OTHER PUBLICATIONS

Kung et al. (2005) Antimicrob Agents and Chemotherapy 49(20: 760-766 (Year: 2005).*
Lahuerta Zamora et al. (2012) J Royal Soc Interface 9: 1892-1897 (Year: 2012).*
AliFax SRL, "Alfred 60$^{AST}$—First Automated System for Bacterial Culture and Susceptibility Testing", Alifax SRL, Italy (2015) 2 pages.
Antimicrobial Susceptibility Test (LAB-1), Faculty of Veterinary Science, Chulalongkorn University, at least as early as Jun. 22, 2015.
Baker, Zelma et al., "The Bactericidal Action of Synthetic Detergents", Walter G. Zoller Memorial Dental Clinic, the Department of Bacteriology and Parasitology, and the Department of Medicine, The University of Chicago (1941) pp. 611-620.
BD Diagnostics, "BD Phoenix, Automated Microbiology System" (2008) 13 pages.
BD Diagnostics, "BD Phoenix ID/AST Manual Panel Inoculation" (2012) 1 page.
BD Phoenix, Laboratory Procedure, pp. 1-30, at least as early as Jun. 13, 2014.

(Continued)

*Primary Examiner* — Blaine Lankford
(74) *Attorney, Agent, or Firm* — Fay Sharpe LLP

(57) ABSTRACT

A method for determining the antimicrobial susceptibility of a microorganism in a clinical sample includes removing a test aliquot from a clinical sample culture before the culture reaches 0.5 McFarland units and isolating the microbial cells. The cells are transferred into a suitable culture medium for microbial growth and an AST assay is performed using the isolated microbes. The concentration of microbial cells in the microbial cells used to set up the AST assay is measured before measuring the degree of microbial growth in different conditions of the AST assay. Devices for determining the anti-microbial susceptibility of a microorganism in a clinical sample are also disclosed.

27 Claims, 7 Drawing Sheets

(56) References Cited

Figure 1:
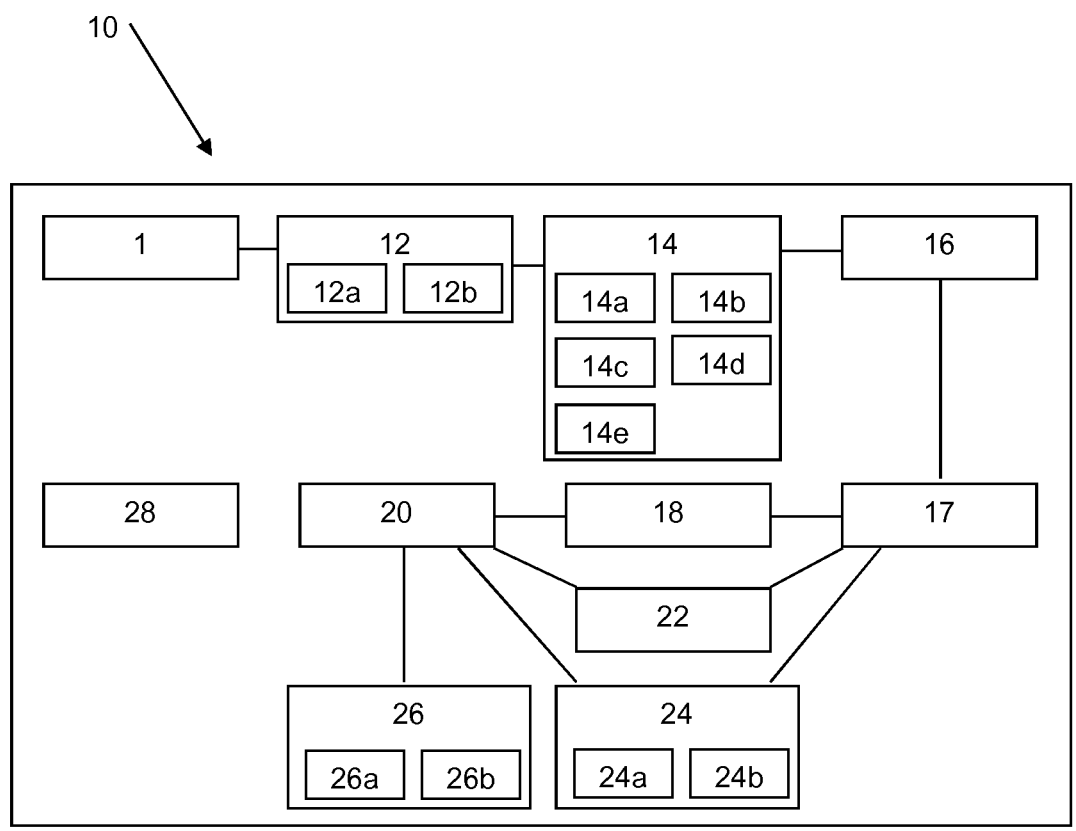

OTHER PUBLICATIONS bioMerieux SA, "Vitek 2 Instrument User Manual" (2008) 218 pages.

Brannon, Patricia et al., "Large-Scale Clinical Comparison of the Lysis-Centrifugation and Radiometric Systems for Blood Culture", Journal of Clinical Microbiology, vol. 22, No. 6 (1985) pp. 951-954.

Broeren, M. A. C. et al., "Antimicrobial Susceptibility Testing in 90 Min by Bacteria Cell Count Monitoring", Clinical Microbiology and Infection, vol. 19, No. 3 (2013) pp. 286-291.

Dahl, Fredrik et al., "Circle-To-Circle Amplification for Precise and Sensitive DNA Analysis", PNAS, vol. 101, No. 13 (2004) pp. 4548-4553.

Fredborg, Marlene et al., "Real-Time Optical Antimicrobial Susceptibility Testing", Journal of Clinical Microbiology, vol. 51, No. 7 (2013) pp. 2047-2053.

Gyarmati, Peter et al., "Simultaneous Genotyping of All Hemagglutinin and Neuraminidase Subtypes of Avian Influenza Viruses by Use of Padlock Probes", Journal of Clinical Microbiology, vol. 46, No. 5 (2008) pp. 1747-1751.

Kagan, Robert L. et al., "Rapid Automated Diagnosis of Bacteremia by Impedance Detection", Journal of Clinical Microbiology, vol. 5, No. 1 (1977) pp. 51-57.

Ke, Rongqin et al., "Colorimetric Nucleic Acid Testing Assay for RNA Virus Detection Based on Circle-To-Circle Amplification of Padlock Probes", Journal of Clinical Microbiology, vol. 49, No. 12 (2011) pp. 4279-4285.

Kesberg, Anna Isabella et al., "Improved Protocol for Recovery of Bacterial DNA From Water Filters: Sonication and Backflushing of Commercial Syringe Filters", Journal of Microbiological Methods, 93, 2 (2013) pp. 1-7.

Lahanas, Sophie et al., "Evaluation of the Alfred 60/AST as a Screening Test for Urinary Tract Infections", Journal of Clinical Microbiology (2013) pp. 1-13.

Loonen, Anne J. M. et al. "Comparison of Pathogen DNA Isolation Methods From Large Volumes of Whole Blood to Improve Molecular Diagnosis of Bloodstream Infections", PLOS ONE, vol. 8, Issue 8 (2013) pp. 1-7.

Lorenz, Michael, "SelectNA Plus—Walk-Away Automated Extraction of Microbial DNA From Clinical Samples", Molzym GmbH & Co. KG, Molzym's Tapas Symposium Direct Molecular Testing (2014) pp. 1-6.

Metzger, S. et al., "Direct Identification of Methicillin Resistant *Staphylococcus aureus* (MRSA) Using Small Numbers of Immobilized Cells and Response to Oxacillin (OXA) by Automated Growth Analysis", ASM, Accelr8 Technology Corporation (2007), 1 page.

Metzger, S. et al., "Rapid Identification of Resistance Phenotypes in Gram-Negative Bacilli Using Automated Digital Microscopy", ASM, Accelr8 Technology Corporation (2009), 1 page.

Metzger, S. et al., "Same-Day ID and Resistance Phenotyping Directly From Respiratory Specimens by Automated Microscopy", ASM, Accelr8 Technology Corporation (2011), 1 page.

Metzger, S. et al., "Rapid Simultaneous Identification and Quantitation of *Staphylococcus aureus* and Pseudomonas Aeruginosa Directly From Bronchoalveolar Lavage Specimens Using Automated Microscopy", Diagnostic Microbiology and Infectious Disease, 79 (2014) pp. 160-165.

Mezger, MSc, Anja et al., "Rapid Antibiotic Susceptibility Testing for Urinary Tract Infections", Uppsala Universitet, Science for Life Laboratory, 1 page, at least as early as Jun. 13, 2014.

Pezzlo, M. T. et al., "High Recovery of Bacteria and Fungi in Low Concentrations From Liquid Samples", Pocared Diagnostics 2064, 7 pages, at least as early as Jun. 13, 2014.

Prere, M.-F. et al., "Rapid Identification of Bacteria, mecA and Van Genes From Blood Cultures", Pathologie Biologie 55 (2007) pp. 375-377.

Price, Connie S. et al., "Rapid Antibiotic Susceptibility Phenotypic Characterization of *Staphylococcus aureus* Using Automated Microscopy of Small Numbers of Cells", Journal of Microbiological Methods, 98 (2014) pp. 50-58.

Sage, Jr., Burton H. et al., "Rapid Visual Detection of Microorganisms in Blood Culture", Journal of Clinical Microbiology, vol. 20, No. 1 (1984) pp. 5-8.

Siemens, "MicroScan Dried Conventional Gram Negative Panels", Siemens Healthcare Diagnostics (2012) 4 pages.

Spezzotti, Gianpiero, "Technical Notes on the Correct Configuration of the Alfred 60/AST Device for the Detection of Urinary Tract Infections", Journal of Clinical Microbiology, vol. 52, No. 5 (2014) pp. 1805-1806.

Sullivan, Nadine M. et al., "Practical Aerobic Membrane Filtration Blood Culture Technique: Development of Procedure", Journal of Clinical Microbiology, vol. 1, No. 1 (1975) pp. 30-36.

Sullivan, Nadine M. et al., "Practical Aerobic Membrane Filtration Blood Culture Technique: Clinical Blood Culture Trial", Journal of Clinical Microbiology, vol. 1, No. 1 (1975) pp. 37-43.

Tenover, Fred C. et al., "Vancomycin-Resistant *Staphylococcus aureus* Isolate From a Patient in Pennsylvania", Antimicrobial Agents and Chemotherapy, vol. 8, No. 1 (2004) pp. 275-280.

van Belkum, Alex, et al., "Next-Generation Antimicrobial Susceptibility Testing", Journal of Clinical Microbiology, vol. 51, No. 7 (2013) pp. 2018-2024.

Wahl, K.L. et al., "Analysis of Microbial Mixtures by Matrix-Assisted Laser Desorption/Ionization Time-of-Flight Mass Spectrometry", Anal Chem. (2002) 15;74(24):6191-9 (Abstract Only).

Whittier, S. et al., "Evaluation of the BD Phoenix Automated Microbiology System for Antibiotic Susceptibility Testing of *Streptococcus pneumoniae*", American Society for Microbiology 106th General Meeting (2006) 4 pages.

Wiles, T. et al., "Rapid Antimicrobial Susceptibility Testing in Phoenix", American Society for Microbiology 99th General Meeting (1999) 3 pages.

Wu, S.-J. et al., "Preparation of Milk Samples for PCR Analysis Using a Rapid Filtration Technique", Journal of Applied Microbiology, 96 (2004) pp. 1342-1346.

Zierdt, Charles H. et al., "Development of a Lysis-Filtration Blood Culture Technique", Journal of Clinical Microbiology, vol. 5, No. 1 (1977) pp. 46-50.

Zierdt, Charles H., "Blood Lysing Solution Nontoxic to Pathogenic Bacteria", Journal of Clinical Microbiology, vol. 15, No. 1 (1982) pp. 172-174.

Zierdt, Charles H. et al., "Lysis-Filtration Blood Culture Versus Conventional Blood Culture in a Bacteremic Rabbit Model", Journal of Clinical Microbiology, vol. 15, No. 1 (1982) pp. 74-77.

Zierdt, Charles H., "Simplified Lysed-Blood Culture Technique", Journal of Clinical Microbiology, vol. 23, No. 3 (1986) pp. 452-455.

Rinsho Byori. The Japanese Journal of Clinical Pathology, vol. 55, No. 7, Jul. 2007, Y. Matsukawa, et al., "Multicenter-evaluation of optimal cell density to determine antimicrobial susceptibility for Haemophilus influenzae by the automated RAISUS system when the early-harvested bacterial cells were used", pp. 611-618; see English language Medline abstract accession No. NLM17718056.

Zhonghua Weishengwuxue He Mianyixue Zazhi, vol. 31, No. 3, Mar. 2011, Y. Tian, et al., "Rapid identification and susceptibility testing of positive blood culture caused by gram negative bacteria", pp. 220-224; see English language Biosis abstract (accesion No. PREV201100310815).

J. Clin Microbial., vol. 45, No. 12, 2007, J-L Donay, et al., "Evaluation of the Inoculation Procedure Using a 0.25 McFarland Standard for the BD Phoenix Automated Microbiology System", pp. 4088-4089.

International Search Report and Written Opinion of International Application No. PCT/EP2016/063952 dated Sep. 9, 2016, 10 pages.

United Kingdom Search Report of Application No. GB 1511129.7 dated Oct. 30, 2015, 6 pages.

* cited by examiner

FIG 3A
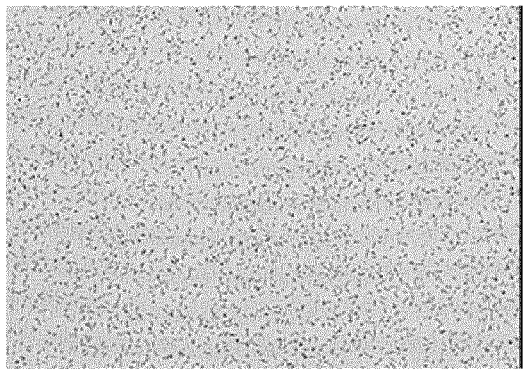
FIG 3B
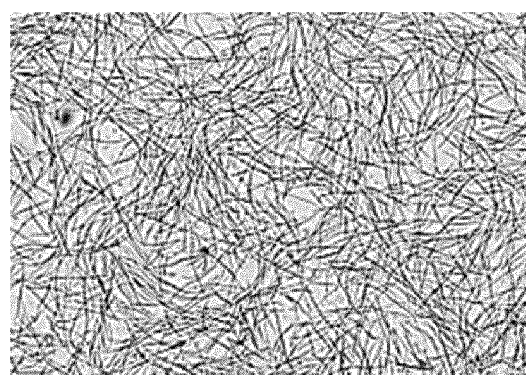
FIG 3C
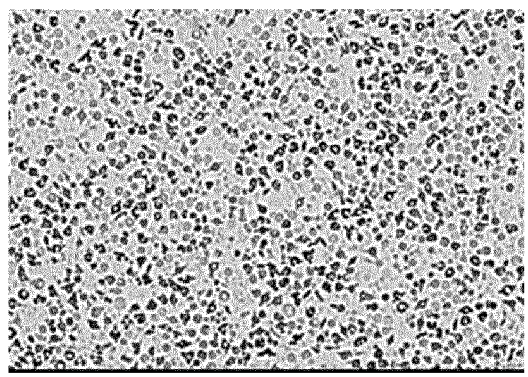
FIG 3D
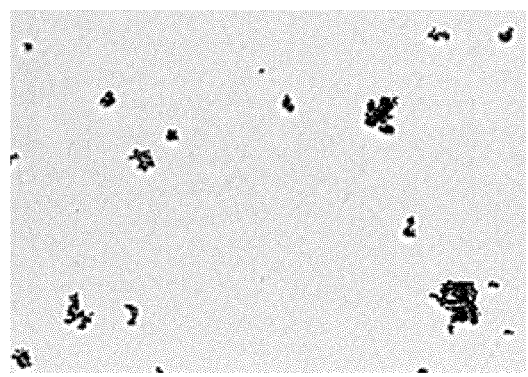
Figure 3

Lane A

Lane B

[Gentamycin]

Lane A

Lane B

[Gentamycin]

FIG 7A
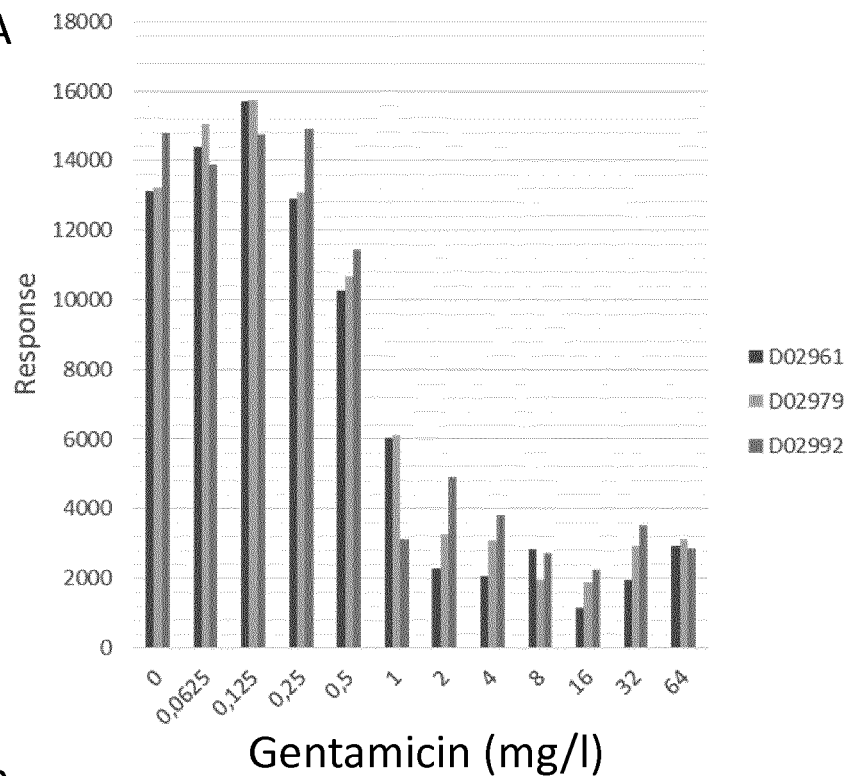
FIG 7B
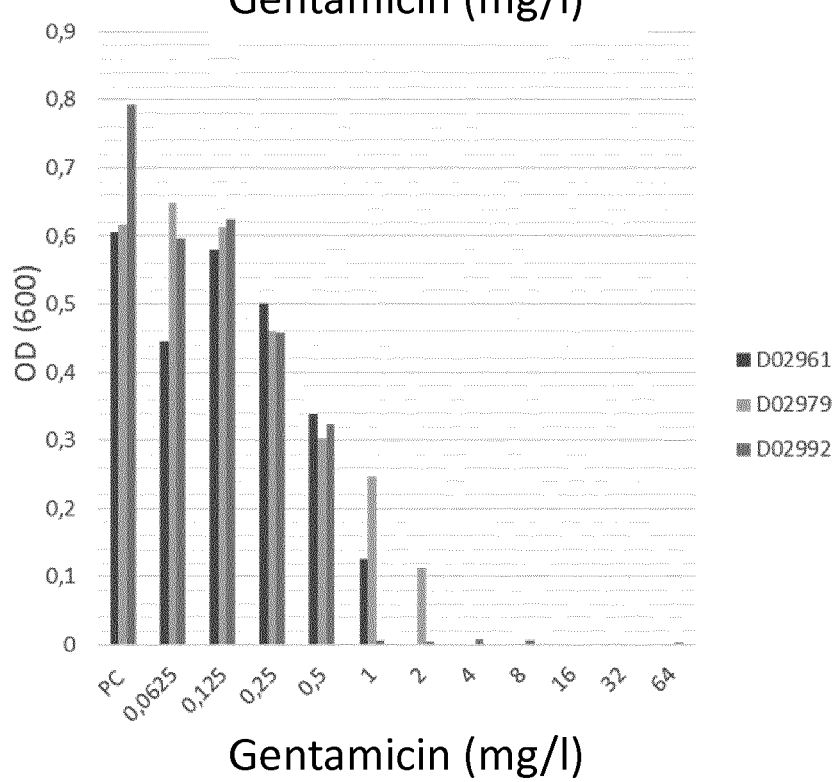
Figure 7

METHOD FOR DETERMINING ANTIMICROBIAL SUSCEPTIBILITY OF A MICROORGANISM

The present invention relates generally to the detection and characterisation of a microorganism in a clinical sample. In particular, the present invention provides a rapid method for performing an antibiotic susceptibility test (AST) on a microorganism from a clinical sample.

Microbial infections represent a major class of human and animal disease with significant clinical and economic implications. Whilst various classes and types of antimicrobial agents are available to treat and/or prevent microbial infections, antimicrobial resistance is a large and growing problem in modern medicine. The numbers of antimicrobial-resistant strains of various microbial pathogens have proliferated in the past 20 years, and microorganisms continue to develop resistance to a growing number of antimicrobial, particularly antibiotic, classes. With the spread of resistance mechanisms to more organisms, the public health impact and costs associated with antimicrobial resistance are projected to increase rapidly in the years to come. In the context of treatment of a microbial infection, it can therefore be desirable, and indeed important, to have information regarding the nature of the infecting microorganism and its antimicrobial susceptibility profile in order both to ensure effective treatment and also to reduce the use of unnecessary or ineffective antibiotics and thereby to help control the spread of antibiotic, or more generally antimicrobial, resistance. This is particularly so in the case of serious or life-threatening infections in which rapid effective treatment is vital.

Sepsis, a potentially fatal whole-body inflammation caused by severe infection is the most expensive condition and driver of hospital costs in the US, comprising 5% of the total national hospital cost. Mortality increases 7% for every hour for severe sepsis, if not treated properly, and the rising prevalence of antimicrobial-resistant sepsis causing strains makes predictions of the correct treatment for sepsis increasingly difficult. The current gold standard for diagnosis of the microorganisms causing sepsis or other infections is based on phenotypic and biochemical identification techniques which require the isolation and culture of pure cultures of the infecting microorganisms. It can take several days to perform the microbial identification (ID) and antibiotic susceptibility (AST) tests to identify the infection and determine the susceptibility profile of the microorganism, which may be resistant to one or more antibiotics. An AST assay provides a 'minimum inhibitory concentration' or 'MIC' value for each antimicrobial agent tested on a microorganism, and can thus provide information on which antimicrobial agents may be effective against the microorganism. Current clinical practice requires treatment with a broad-spectrum antibiotic within 1 hour of suspicion of sepsis based on clinical symptoms. A second dose is required within 6-8 hours and this administration is continued every sixth to eighth hour until identification of the microorganism and its antibiotic susceptibility (ID/AST) is established.

Due to the lethal condition of sepsis physicians are unwilling to change treatment from broad-spectrum antibiotics initially if the patient experiences a clinical response until the nature of the microbial infection is determined and antimicrobial susceptibility established. This in turn leads to the unnecessarily high use of broad spectrum antibiotics, in turn fuelling the rise of antimicrobial resistance among microorganisms.

Conventional testing methods utilise turbidity measurements or disc diffusion to assess the effect of antimicrobial agents on microorganism growth, and traditional biochemical and microbiological techniques to identify a microorganism. These techniques can take several days to identify and characterise a microorganism in a clinical sample, due to the requirement for prolonged periods of incubation to allow microbial growth. There is thus a requirement for techniques that can rapidly identify microorganisms and determine the antimicrobial susceptibility profile of antimicrobial resistant microorganisms, and various different techniques that reduce the time between sample collection and diagnosis have been developed in recent years.

Methods of enriching microorganisms in a clinical sample that bypass the requirement for long periods of incubation are described in U.S. Pat. No. 8,481,265; microbial cells can be enriched from clinical samples by the selective lysis of non-microbial cells, enriching the concentration of microbial cells in a sample and bypassing the requirement for prolonged incubation prior to testing a sample.

Methods of rapid microbial identification are described in US 2010/0124763, in which microbial cultures are enriched and microorganisms identified spectroscopically.

Rapid susceptibility testing techniques using flow cytometry (Broeren et al. 2013 Clin Microbiol Infect 19, 286-291) and automated microscopy (Price et al. 2014 JMM. 98 50-59) have been developed to reduce the time required for incubation prior to susceptibility being determined. The systems developed by Accelerate Diagnostics use imaging of the growth of individual cells or colonies on a surface to monitor microbial growth in the presence of an antibiotic in AST tests (see for example WO2014/040088, US 2014/0278136 and U.S. Pat. No. 8,460,887). Quantitative PCR of microbial DNA has also been used as a measure for microbial growth to determine antimicrobial susceptibility, as described in U.S. Pat. No. 5,789,173.

Combined microorganism identification and susceptibility testing methods have also been developed. Described in US 2005/0095665 is a system in which panels of selected growth media and chromogenic and fluorogenic substrates are used in combination with turbimetric measurement of microbial growth in an automated microtititer well format to identify microorganisms and determine antimicrobial susceptibility. Automated microscopy methods have also been developed (Metzger et al. 2014 Diagnostic Microbiology and Infectious Disease 79 160-165). The BD Phoenix™ system also allows for the rapid simultaneous identification and characterisation of microorganisms, and utilises a variety of chromogenic and fluorogenic substrates to identify microorganisms in a sample and monitor microbial growth to determine the antimicrobial susceptibility of microorganisms in a sample.

However, despite these developments in the field of antimicrobial susceptibility testing, there is an ongoing requirement for new and improved methods of antimicrobial susceptibility testing, including methods which are simple to perform and susceptible to automation and which allow rapid AST determination.

Generally speaking, results obtained for AST determinations in the clinical field should be comparable between different methods and/or different clinical laboratories. To this end it is customary to use prescribed and recognised conditions for AST testing. This may involve the use of prescribed medium (e.g. Muller-Hinton (MH) media) and culture conditions. In particular, it is also customary to use standardised microbial titres (i.e. a standardised (or standard) number or amount (e.g. concentration) of microbial cells) to set up the cultures which are performed (i.e. monitored for growth) in an AST test, such that the number or amount of bacteria in the cultures is at a set value. For example, McFarland standards are conventionally used as a reference to adjust the turbidity of microbial suspensions (especially bacterial suspensions) so that the number of microorganisms in the culture preparation used to set up the cultures will be within a given range to standardise microbial testing, including particularly AST testing, and thus the number of microorganisms in the test microbial cultures will also be known. McFarland standards are set based on the turbidity of reference suspensions, and microbial suspensions are adjusted in concentration (or number of bacteria) to match the turbidity of a selected McFarland standard.

Typically in the methods of the art, a microbial culture (i.e. a clinical sample culture) is allowed to grow until a positive culture result is obtained in a culture monitoring system. In automatic culture detection systems such as e.g. Bactec or Bact/Alert systems the concentration of bacteria needed to be indicated as positive is between $10^8$ to $10^9$ CFU/ml, corresponding to 0.5 to 3.5 McFarland units (if measured in a saline solution). The lowest McFarland value that is readily detectable (either by eye or by turbidimetric measurements) is around 0.5 McFarland units. ID tests and AST determination may then be performed.

For an AST test, it is typical to prepare a further culture from the clinical sample culture (e.g. a positive culture) to use as, or for preparing, an inoculum for the AST test cultures and to standardise such an inoculum to a pre-set microbial concentration or McFarland value (typically 0.5 McFarland units) before it is used to inoculate the AST test cultures. Thus inocula for AST are typically prepared using, or starting from, cultures or microbial suspensions which are at 0.5 McFarland units.

Conventionally, microbial cells to be tested for AST (e.g. from a clinical sample culture) are plated to obtain isolated colonies. Colonies may then be collected and used to prepare a microbial cell suspension for use as the inoculum. The turbidity of the microbial suspension may be adjusted to 0.5 McFarland before use. Alternatively, the isolated individual colonies may be used to inoculate a culture medium which may be cultured to provide the inoculum. The culture may be allowed to grow to the desired (0.5 McFarland) standard and/or may be adjusted if necessary to this standard, before it is used as the inoculum. Thus before normalizing the concentration of bacteria before an AST, microbial cultures are typically allowed to grow until the growth reaches a turbidity equal to or greater than that of a 0.5 McFarland standard. If needed, the culture may be adjusted to give culture having a turbidity equivalent to the 0.5 McFarland standard. This may then be used as the inoculum that is used to set up an AST assay. Alternatively, microbial cells from a positive culture may be plated to provide individual microbial colonies, which may be resuspended in a microbial suspension, and optionally be cultured, to provide a suspension of at least 0.5 McFarland units. This may be used as the inoculum to set up an AST assay. The inoculum obtained at this point (i.e. the culture or suspension of approximately 0.5 McFarland units) is diluted in broth to give the desired standardised final cell number concentration used for an AST culture. By way of reference, a microbial culture/suspension of 0.5 McFarland units comprises a microbial concentration of approximately $1 \times 10^8$ CFU/ml. Such a microbial culture/suspension would typically be diluted in broth by a factor of ~200 when setting up an AST culture, i.e. each AST culture condition would typically comprise a starting microbial concentration of approximately $5 \times 10^5$ CFU/ml.

The present invention seeks to provide an improved workflow which may provide information regarding the antimicrobial susceptibility of a microorganism in a clinical sample more rapidly than is currently possible using conventional testing systems. In particular, the present invention eliminates the need to wait for a culture to reach a level of at least 0.5 McFarland units before antimicrobial susceptibility may be determined. Further, it does not require the use of standardised microbial titres or concentrations in the AST test. Advantageously this may allow also lower microbial concentrations to be used in the AST test, or indeed different concentrations to be used, depending on the precise circumstances and nature of the test (e.g. for different microorganisms and/or antibiotics under investigation), as long as the concentration used is known.

It is not required according to the present invention to wait until a clinical sample culture has reached 0.5 McFarland units, or indeed to grow a clinical sample culture to any particular, e.g. McFarland, standard. Thus, it is not required to wait until the clinical sample culture has reached a pre-defined or particular stage of growth. This allows the determination of antimicrobial susceptibility to be initiated earlier than is currently possible. In automatic culture detection systems such as e.g. Bactec or Bact/Alert systems the concentration of bacteria needed to be indicated as positive is between $10^8$ to $10^9$ CFU/ml, corresponding to 0.5 to 3.5 McFarland, if they had been in a saline solution. At this point, further tests are initiated.

Accordingly, the present invention also allows the determination of antimicrobial susceptibility to be achieved before the clinical sample culture reaches 0.5 McFarland units, and before the culture would be deemed to indicate a "positive" culture. This means that a clinical sample culture grown for AST testing according to the methods of the present invention need not be cultured for so long before an AST test is initiated, leading to a more rapid procedure. Whereas the methods of the prior art typically isolate microbes from a very rich source, e.g. a positive blood culture flask, urine sample or lung punctates, aspirates or drainages in order to set up cultures for testing antimicrobial susceptibility, the present invention provides methods for determining the antimicrobial susceptibility of microorganisms in a clinical sample which comprises a lower concentration of microorganisms (i.e. which has a lower concentration of microorganisms to start with) or using cultures of the clinical sample which comprise a lower concentration of microorganisms. For example, cultures of the clinical sample comprising lower concentrations of microorganisms may be used to set up the AST tests. In particular, the present invention provides a method for determining the antimicrobial susceptibility of a microorganism in a clinical sample before the culture vessel reaches 0.5 McFarland units. Thus, the present invention may also be seen to provide a method for determining the antimicrobial susceptibility of a microorganism in a clinical sample before a positive culture (e.g. a positive blood culture flask) is confirmed.

In many microbial testing procedures as carried out today, antimicrobial susceptibility tests take place only once there has been a "positive" result in a microbial culture, namely once microbial growth has been detected in a culture or growth test (a positive culture test). Thus for example, a blood or other sample is introduced to a culture vessel (e.g. a blood culture flask), and this is cultured. The culture system is designed or selected to indicate that (when)

microbial growth has occurred, for example by including an indicator substance that yields a signal dependent on microbial growth (e.g. due to pH change, or conversion/consumption of a substrate, or generation of microbial metabolic product etc.) or simply by detecting microbial growth by any means (including for example by turbidimetry). For example, microbial growth may be allowed to continue until the culture reaches a level of at least 0.5 McFarland units. When/if sufficient microbial growth occurs to yield a signal/give detectable growth, this indicates a "positive" result in the culture/microbial detection (i.e. that there is growth of a microorganism in the clinical sample. As indicated above, in one embodiment a "positive" culture result may be considered as equivalent to about 0.5 McFarland units.

Although it may not be known when a positive culture result is obtained what is the identity of the microorganism, it is generally required that this is established before the antimicrobial susceptibility of a microorganism may be determined, as the identity of the microbe is needed in order to choose the correct antimicrobials and culture conditions to be tested in the AST assay. Traditionally, the identity of the microbe is determined using microscopy and/or biochemical testing, whereas molecular techniques and MALDI-TOF are increasingly being used for more rapid identification of a microorganism in a clinical sample or spectral identification such as described in e.g. U.S. Pat. No. 8,652,800. The identification process may take some hours e.g. 1, 2, 3, 4, 6, 8, 10 or 12 hours or more, to perform. However, identification of a microorganism in a clinical sample is typically determined separately from the cultured clinical sample, and AST is typically only performed in methods of the art once a positive culture result has been obtained for the clinical sample culture. Once a positive culture is reached and the ID is known, the AST assays can be performed.

In contrast to this, the methods of the present invention may be initiated once (or as soon as) the ID of the microorganism in the clinical sample is determined, and do not require the clinical sample culture to have reached 0.5 McFarland units (or a positive culture result). Thus, it is possible to initiate the methods of the present invention immediately after the ID of the microorganism in a clinical sample has been determined. Preferably, the ID determination method will be capable of determining the identity of a microorganism in a sample rapidly (i.e. within 1, 2, 3, 4, 6, 8, 10 or 12 hours as discussed above, preferably within 7 hours, e.g. using a molecular-based or mass spectrometry (MS)-based identification assay), and particularly before a positive culture result is obtained. Advantageously, a sample (i.e. portion or aliquot) of the clinical sample culture may be taken in order to determine the ID of the microorganism therein, whilst the remainder of the clinical sample culture is incubated further whilst the ID determination is performed. Methods for the parallel identification and determination of antibiotic susceptibility of a microorganism are taught in the co-pending application with publication number WO2015/189390.

The present invention accordingly in one embodiment has the advantage that it is not necessary to wait until a positive result in a culture test has been obtained, meaning that antimicrobial susceptibility may be more rapidly determined. In particular the present invention has the advantage that one need only wait until a positive ID has been obtained for the microorganism in the clinical sample (i.e. once the presence and identity of a microorganism in a sample has been established) before an antimicrobial susceptibility assay may be performed. In this regard, the clinical sample need only be incubated for such a period of time as is required to for a positive ID to be obtained (i.e. to identify the microorganism present in the clinical sample) before a test aliquot is taken to determine antimicrobial susceptibility. Advantageously, the period of time required to determine the identity of a microorganism in the sample will be shorter than the period of time required in order to obtain a level of 0.5 McFarland units in a culture test. The methods of the present invention may thus be performed before this set level of growth is obtained in a culture test (e.g. before the culture reaches a level of 0.5 McFarland units). In other words, a culture of the clinical sample to provide cells for an AST test is grown/cultured for a period of time which is less than that required to obtain a microbial concentration equivalent to 0.5 McFarland units.

The methods of the present invention rely on the isolation and enrichment of microbial cells from a culture of the clinical sample. In particular, a selective lysis is carried out of cells derived from the subject from whom the clinical sample is taken (i.e. the subject under test) that are present in a clinical sample or cultured clinical sample, and the microbial cells obtained therefrom are subsequently transferred into culture medium to provide a microbial culture preparation. This is then used as the inoculum for the AST tests.

Notably, the selective lysis method described herein will be performed on an aliquot of a clinical sample culture, which culture has not yet reached 0.5 McFarland units. Thus, the selective lysis of cells derived from the subject under test is effected at an earlier time point than is performed in the methods of the art, and thus the microbial culture preparation may be obtained at an earlier point in time. Indeed, this step may be performed without measuring the abundance or concentration of microbial cells in the clinical sample culture, and may be initiated once the ID of the microorganism is obtained (the culture may by this stage have reached any value below 0.5 McFarland units).

The concentration of microbial cells present in the microbial culture preparation may be measured at this stage, and optionally or if necessary adjusted, before it is used to set up an AST assay. Alternatively, once the microbial culture preparation is established, an AST assay may be set up directly from the microbial culture preparation (and the starting concentration of microbial cells may be measured in test microbial cultures at the start point of the AST assay). It will we seen therefore that the methods of the present invention are based on the assumption that a concentration below 0.5 McFarland in the clinical sample culture is sufficient to provide microbial cells for an AST test.

Advantageously, the present invention thus provides a workflow in which the concentration of microorganisms present in a sample (e.g. in a culture medium or culture) may be determined at an earlier time point than is currently possible in the art, allowing for an AST assay to be performed at an earlier time point. In other words, although the concentration of microorganisms is first established at a later stage in the method (i.e. immediately before, or during the setting up of test microbial cultures, rather than waiting for the clinical sample culture to reach 0.5 McFarland units), the total period of elapsed time from obtaining a clinical sample to setting up an AST assay having test microbial cultures with a known concentration of microbial cells, is significantly reduced. Thus, the antimicrobial susceptibility of a microorganism may be established sooner.

Accordingly, in one aspect the present invention provides a method for determining the antimicrobial susceptibility of a microorganism in a clinical sample, said method comprising:
- a) providing a clinical sample culture of a clinical sample in a culture vessel containing culture medium;
- b) removing a test aliquot from said clinical sample culture in said culture vessel, wherein said aliquot is removed when the culture in the culture vessel is less than 0.5 McFarland units;
- c) selectively isolating microbial cells from said test aliquot;
- d) transferring said isolated microbial cells into a culture medium suitable for microbial cell growth thereby to prepare a microbial culture preparation;
- e) inoculating a series of test microbial cultures for an antibiotic susceptibility test (AST) using the microbial culture preparation of step (d), wherein the series of test microbial cultures comprises at least two different growth conditions, wherein the different growth conditions comprise one or more different antimicrobial agents, and each antimicrobial agent is tested at two or more different concentrations;
- f) assessing (e.g. monitoring) the degree of microbial growth in each growth condition;

wherein the concentration of microbial cells in said microbial culture preparation is determined between steps (d) and (e) and/or the concentration of microbial cells is determined in the test microbial cultures during or after step (e) but prior to step (f), and optionally or if necessary the concentration of microbial cells in said microbial culture preparation and/or said test microbial cultures is adjusted to a predetermined or desired value; and wherein the degree of microbial growth in each growth condition is used to determine at least one MIC value for at least one antimicrobial agent, thereby to determine the antimicrobial susceptibility of said microorganism in said clinical sample.

As discussed in more detail below, the clinical sample may typically comprise cells from the subject under test (that is the test subject from whom the clinical sample is obtained). Accordingly, it is typically a cell-containing clinical sample (that is a "host cell"-containing clinical sample). In a preferred embodiment the clinical sample is blood, or a blood-derived product, especially blood. The clinical sample culture is accordingly preferably a blood culture, for example a blood culture flask (BCF) as is typically used in clinical practice today to collect and/or culture blood samples. It may also be a sub-culture of a primary blood culture (i.e. a subculture from a BCF). It may be the same or a different culture to one that is used for a microbial identification (ID) test. For example, one or more than one (e.g. parallel) cultures may be set up from a clinical sample. Thus one culture may be used for ID and another may be used for AST (once the ID result is known). In one embodiment, it is preferred for the same clinical sample culture to be used for both ID and AST.

Advantageously, the clinical sample culture of step (a) is a liquid culture, that is the culture medium of step (a) is a liquid culture medium and the aliquot removed in step (b) is removed as a liquid test aliquot.

Although typically the clinical sample culture will be a clinical sample added to a culture medium which will have been subjected to a period of culture (e.g. in a cell culture apparatus), it is also possible to prepare a clinical sample culture by separating and removing microbial cells from a clinical sample, directly (e.g. straight from a clinical sample) or indirectly (e.g. from a treated or processed clinical sample, for example a sample added to a diluent or some other medium, e.g. EDTA-blood), and adding (e.g. resuspending) the separated microbial cells into a culture medium in a culture vessel. Thus, a clinical sample culture may be a suspension of microbial cells separated, or obtained, from a clinical sample.

From the above discussion, it will be apparent that the clinical sample culture of step (a) does not reach 0.5 McFarland units before a test aliquot is taken from the culture, or the culture is otherwise less than 0.5 McFarland units. Thus the test aliquot in step b) may be removed before the clinical sample culture reaches 0.5 McFarland units, for example before the clinical sample culture has been cultured for long enough to reach 0.5 McFarland units. The test aliquot may thus be removed before clinical sample culture reaches, or before the clinical sample has been cultured for long enough to reach, 0.30, 0.25, 0.20, 0.10, 0.05, 0.01, 0.005, 0.001, 0.0005, or 0.0001 McFarland units, or the equivalent thereof. McFarland units are units for measurement of turbidity within a microbial culture, and a series of McFarland standards having different McFarland units is commercially available, and may be used to calibrate any detection device which requires a particular McFarland value to be measured. A culture having a value of 0.5 McFarland units typically comprises approximately $10^8$ CFU/ml (colony-forming units per millilitre), and thus the concentration of microbial cells in the clinical sample culture at the time that the test aliquot is removed will be less than this value, for example, less than $5 \times 10^7$ CFU/ml, less than $10^7$ CFU/ml, less than $5 \times 10^6$ CFU/ml, less than $10^6$ CFU/ml, more particularly less than $5 \times 10^5$ CFU/ml, less than $10^5$ CFU/ml, and most particularly less than $5 \times 10^4$ CFU/ml or less than $10^4$ CFU/ml, less than or equal to $5 \times 10^3$ CFU/ml or less than or equal to $10^3$ CFU/ml, or less than $10^3$ CFU/ml, e.g. less than or equal to $5 \times 10^2$ CFU/ml or less than or equal to $10^2$ CFU/ml. The amount of microbial cells present in the clinical sample culture may be determined in terms of CFU/ml and this may be converted to, or represented by a McFarland unit value. A given CFU/ml value may thus be regarded as equivalent to a given McFarland unit value.

Thus, a microbial culture having a particular McFarland value will typically comprise a certain concentration of microbial cells (e.g. bacterial cells). As discussed above, a value of 0.5 McFarland units is the lowest value that may be associated with a "positive" culture result in an automatic culture detection system, however, a "positive culture" corresponds to 0.5 to 3.5 McFarland units. Thus in one embodiment the clinical sample culture is a "non-positive" culture.

In accordance with the description above, the culture of step (a) has not yet reached a positive result (or been cultured to the point that a positive result may be obtained). A positive result is an indication that a culture may be scored as positive in a culture test for microbial growth, i.e. has reached a particular level of growth. "Non-positive" accordingly means that the period of time for which the clinical sample culture has been cultured (i.e. incubated under culture conditions, or otherwise maintained in a condition which allows or is permissive to microbial growth) is shorter, or less, than that which is necessary or required for a positive culture test result. A "non-positive" culture would typically not have reached 0.5 McFarland units. A culture may thus be viewed as "non-positive" until it reaches 0.5 McFarland units. Thus, a test aliquot is removed (or is first removed) in step (b) before the culture reaches 0.5 McFarland units, i.e. before a positive result is obtained or obtainable in a culture test i.e. before a positive culture test result is obtained or before the time that would be required to obtain a positive culture result. Rather than awaiting a positive culture result, a test aliquot may be taken in the methods of the present invention once a positive ID has been obtained for the microorganism in the clinical sample. As a positive ID may be obtained before the culture reaches 0.5 McFarland units (i.e. a non-positive culture), the test aliquot may thus be taken (and the selective lysis etc. performed) at an earlier stage than would be possible if the culture were to be grown until it reaches 0.5 McFarland units before testing.

As noted above, in another embodiment, a clinical sample culture may be prepared by resuspending microorganisms separated from a clinical sample or clinical sample preparation to an amount of less than 0.5 McFarland units, or less than the CFU/ml values listed above.

As will be described in more detail below, step (c) of selectively isolating microbial cells from the test aliquot may be performed by positive or negative selection of microbial cells. As noted above, the clinical sample may typically comprise cells from the test subject. Thus step (c) can be viewed as a step of separating microbial from non-microbial cells in the test aliquot. Typically this step may involve selectively lysing any non-microbial cells are present in said test aliquot to obtain a microbial suspension and recovering microbial cells from the microbial suspension.

"Non-microbial cells" in the test aliquot include particularly any cells in the clinical sample/test aliquot which derive from the test subject from whom the clinical sample is obtained. Thus, they are cells from the test subject, or "host" from whom the clinical sample is obtained.

Step (d) may comprise suspending the recovered, or isolated, microbial cells in the culture medium to prepare a microbial culture preparation. The microbial culture preparation obtained at this stage is used as, or to prepare, the inoculum for setting up the test microbial cultures in the AST assay.

As will be discussed in more detail below, the concentration of microbial cells may be determined using any method suitable for assessing microbial growth, including in particular any method described herein, for example in the context of assessing or determining microbial growth in the AST test.

A series of test microbial cultures is set up using the microbial culture preparation of step (d). A step of determining the concentration of microbial cells in said microbial culture preparation may be performed after step (d) to determine whether (or that) there are sufficient, or a suitable number of, microbial cells to perform the AST test of step (e), or in other words to determine whether (or that) the concentration of microbial cells in the microbial culture preparation is sufficient or suitable to perform an AST test.

If the concentration of cells is suitable, then the method may be performed from step (e), that is the AST test may be performed using the microbial culture preparation directly as the inoculum for the AST test cultures. If the concentration of cells is not sufficient or suitable, the concentration of microbial cells in the microbial culture preparation and/or in the test microbial cultures may be adjusted. More particularly the concentration may be adjusted to increase or to decrease the number, or concentration, of microbial cells. As will be discussed in more detail below, the adjustment step may be physical or virtual (e.g. by algorithmic correction).

Thus for example the concentration (or number) of microbial cells in the microbial culture preparation may be physically increased (e.g. by culturing the microbial culture preparation for a period of time to allow the microbial cells to grow) or decreased (e.g. by dilution) prior to inoculating the test microbial cultures, or in the course of inoculating the test microbial cultures (e.g. by selecting an appropriate amount (e.g. volume) to be used to set up the test cultures, either by adding to solid (e.g. freeze-dried antibiotics) or by dilution when a portion or aliquot of the microbial culture preparation is added to a volume of antibiotic and/or culture medium for the AST test. Accordingly the test microbial cultures of step (e) may be inoculated with the microbial culture preparation from step (d) or with an adjusted (e.g. diluted) microbial culture preparation.

Alternatively, the microbial culture preparation may be used to inoculate a series of test microbial cultures without measuring the concentration of microbial cells therein, and instead the concentration of microbial cells in the test microbial cultures may be determined directly. In particular, this may be done if a quantitative or semi-quantitative technique has been used to determine the ID of the microorganism in the clinical sample culture, e.g. a microarray or qPCR, as techniques such as these may provide an initial estimate of the concentration of microbial cells present in the microbial culture preparation. It will be seen, however, that either of these steps may be used to determine the starting concentration of microbial cells present in the test microbial cultures of the AST assay.

A virtual adjustment may take place, using e.g. mathematical methods to account for (e.g. to normalise) the concentration of cells present in the microbial culture preparation or in the test microbial cultures. This may be done using algorithms which can readily be prepared according to methods known in the art. The parameters used to adjust the concentration of microbial cells may be obtained empirically, and will vary depending on the identity of the microorganism and the antimicrobial agent that is being used. For instance, the adjustment may be significant e.g. if a microorganism is known to secrete enzymes which degrade an antimicrobial agent, or if the microorganism forms a biofilm.

The concentration of microbial cells in the microbial culture preparation and/or the test microbial aliquots of the AST assay may thus be adjusted to any desired or predetermined value. This value will differ depending upon whether the adjustment is made to the microbial culture preparation or to the test microbial cultures for the AST test.

In one embodiment, the concentration of microbial cells in the microbial culture preparation will be, or will be adjusted to be, at least 10, $10^2$, $10^3$, $10^4$, $10^5$, $10^6$, $10^7$, $10^8$ or $10^9$ CFU/ml. Preferably the concentration of microbial cells in the microbial culture preparation will be 10-$10^9$, $10^2$-$10^9$, $10^3$-$10^9$, $10^4$-$10^9$ CFU/ml, $10^5$-$10^9$ CFU/ml, $10^6$-$10^9$ CFU/ml, $10^7$-$10^9$ CFU/ml. In one embodiment the microbial culture preparation may be prepared or adjusted to a McFarland standard of 0.5 McFarland (or $10^8$ CFU/ml) to give a "standard" or standardised concentration for use as an AST inoculum, but as discussed, this is not necessary.

The microbial culture preparation is used to inoculate the test microbial cultures. As discussed herein, the microbial culture preparation may be added to culture medium comprising an antibiotic (or a control) to prepare a test microbial culture, i.e. the microbial culture preparation may be diluted at this stage. Thus, the test microbial cultures may be adjusted at this point to comprise any desired or predetermined concentration. Thus, the test microbial cultures will comprise at least 10, $10^1$, $10^2$, $10^3$, $10^4$, $10^5$, $10^6$, $10^7$, $10^8$ or $10^9$ CFU/ml, preferably $10^2$-$10^8$, $10^3$-$10^7$ or $10^4$-$10^6$ CFU/ml. In one embodiment the test microbial cultures for the AST test may comprise $5 \times 10^5$ CFU/ml (i.e. a standard or standardised microbial cell concentration for AST), but this is not necessary.

In certain embodiments the concentration of microbial cells in the, optionally adjusted, microbial culture preparation or in the test microbial culture will be less than the standard/standardised concentrations indicated above.

Standard/standardised conditions for performing AST assays exist as set forth by The European Committee on Antimicrobial Susceptibility Testing (EUCAST) or The Clinical and Laboratory Standards Institute (CLSI) enable MIC values obtained in a particular AST assay to be compared to reference MIC values. However, the present invention allows an MIC value obtained using non-standard/standardised microbial cell concentrations (microbial culture preparations and/or test microbial cultures) to be compared with a reference MIC value.

After any adjustment step, and in particular physical adjustment step, the concentration of microbial cells in the microbial culture preparation may be determined again. Particularly, the concentration of microbial cells may be determined after a step of increasing the microbial cell concentration, e.g. by culturing the microbial culture preparation.

As will be described in more detail below, the assessing or monitoring of microbial growth in step (f) of the AST test may conveniently be performed by visually assessing or imaging the microbial cells, particularly by visually assessing or imaging the amount of microbial cell matter (that is microbial biomass) present in the microbial test culture.

The clinical sample culture may be any culture of the clinical sample. Conveniently, it may be a primary culture of the clinical sample. Thus, the clinical sample may be introduced into a culture vessel containing culture medium and subjected to culture. However, the invention is not limited to this and a secondary or further culture of the clinical sample may also be used. As described in co-pending patent application with publication number WO2015/189390, it may be particularly advantageous for a single sample to be taken from the test subject and for a single sample to be placed into and kept in culture while various microbial identification tests and AST tests are ongoing. A new workflow is described in which molecular ID tests are performed at an early stage of culture, which may lead to more rapid AST tests if microbial identification (ID) is obtained. However, the initial clinical sample is kept in the culture, to permit conventional (e.g. biochemical) ID tests and AST tests to be performed, either to confirm the rapid molecular and AST test results, or in case a positive microbial ID cannot be obtained and rapid AST tests performed. The clinical sample culture may accordingly be such a first clinical sample culture according to this method. However, it is not essential that only a single culture is prepared and incubated (cultured). It is possible that a single initial culture may be set up (e.g. a single culture vessel may be inoculated with the clinical sample) and from this one or more sub-cultures may be set up and a sub-culture of the initial (i.e. first) culture may be used for the AST test according to the present invention. The initial primary culture may be maintained (i.e. maintained in culture) in case further tests are necessary or desirable. Thus, alternatively, the clinical sample culture of step (a) of the present method may be a second (or further) clinical sample culture set up by removing a portion of the first (initial) clinical sample culture or a further preceding culture (removing the portion either before or after a period of culture) and introducing said portion to a second (or further) culture vessel containing culture medium to prepare a second (or further) culture. In a further alternative embodiment, the clinical sample culture may be provided by isolating microbial cells from a clinical sample (e.g. as is performed in step (c) of the present methods) and transferring said cells into a culture medium. For instance, this may be the case where the clinical sample is not provided in a culture medium, e.g. if the clinical sample is collected in an EDTA blood tube. The microbial cells obtained therefrom may be transferred into a culture medium suitable for microbial growth in order to provide the clinical sample culture. In other words, the clinical sample culture may comprise a microorganism that is derived (isolated, enriched or recovered) from a clinical sample, in a culture medium suitable for microbial cell growth, i.e. the clinical sample may first be processed before a clinical sample culture is established.

A key feature of the present invention is the development of a workflow which can isolate microbial cells from a culture of a clinical sample and measure the concentration of microbial cells present in a sample at an early time point. A single initial culture may be set up (e.g. a single culture vessel may be inoculated with the clinical sample) and used in the methods of the present invention, or one or more sub-cultures may be set up, and a sub-culture of the initial culture may also be used. The initial primary culture may be maintained (i.e. maintained in culture) in case further tests are necessary or desirable.

It will be seen that the methods of the invention rely upon selectively isolating, or recovering, microbial cells from the clinical sample culture (or more particularly from the test aliquot which is removed therefrom). Conveniently this may involve first removing any cells which derive from the subject under test (e.g. mammalian cells) present in said test aliquot and recovering the microbial cells therefrom. The microbial cells are transferred into a culture medium suitable for microbial cell growth (e.g. a liquid culture medium). In one embodiment of the present invention, the concentration of microbial cells present in the resulting microbial culture preparation is measured at this stage.

In a first embodiment the microbial culture preparation may be found to comprise a sufficiently high concentration of microbial cells that an antimicrobial susceptibility test (AST) may be set up at this stage. It will be seen therefore that in a preferred aspect, the present invention thereby removes the need for an extended culturing step to take place before AST is performed (e.g. it is not necessary to wait for a positive test culture result in the clinical sample culture). This leads to a faster assessment of the antimicrobial susceptibility of a microorganism in a sample, and can lead to the faster treatment of patients as well as faster out-phasing of unnecessary treatment.

However, if the microbial cell preparation does not comprise a sufficiently high concentration of microbial cells to be used as an inoculum for an AST assay to be performed (which may be determined between steps (d and e)), the method allows for further test aliquots to be taken from the clinical sample culture vessel at subsequent time points, i.e. after a longer period of culture has elapsed, in order that more microbial cells might be obtained before an AST method is performed. Thus, the adjustment step may comprise adjusting the concentration of microbial cells in a microbial culture preparation by preparing a new microbial culture preparation from a further test aliquot (e.g. second test aliquot) removed from the clinical sample culture at a later time (i.e. after a longer period of culture). This longer period of culture may advantageously be less than that required to obtain a positive culture test result. However, although it is less preferred, it is not precluded that any subsequent or additional period of culture of the clinical sample culture is such that the clinical sample culture is cultured for a period of time which is sufficient to obtain a positive culture test result, or longer, as long as the first test aliquot is removed from the clinical sample culture at a period of time which is less than that required to reach 0.5 McFarland units, e.g. to obtain a positive culture test result.

It will accordingly be understood that certain steps of the method of the present invention may be repeated, or performed one or more times, that is to say aliquots may be removed from the clinical sample culture in the culture vessel one or more times. The present invention also allows the continued culture of the clinical sample in the culture vessel whilst the method of the invention is performed, thereby allowing the possibility of repeating the AST assay or of continuing to culture to allow conventional testing.

As is clear from the context, an aliquot of the clinical sample culture removed from the culture vessel may simply be a portion, i.e. a part or fraction of the culture vessel contents. Thus in one, albeit less preferred, embodiment of the present invention, steps (b)-(f) may be repeated, at least once i.e. performed more than once (such as 2, 3, 4, 5 or more times). Alternatively, the test aliquot may be all of the clinical sample culture.

The culturing of the clinical sample in the culture vessel, or any culturing of the microbial culture preparation for adjustment step, or indeed the step of culturing the microbial test cultures in the AST (i.e. the step of culturing the microbial test cultures in step (f) order to monitor microbial growth) may be performed in any convenient or desired way, as described in more detail below. In this regard, culture apparatus for culture of clinical samples for e.g. diagnostic or microbial detection purposes are known and may be used. Different culture apparatus or culture systems may be used for the separate culture of the clinical sample culture in the culture vessel (and/or of the microbial culture preparation in step (d), and/or for the culture required during the AST assay in step (f). Furthermore, as mentioned above and described in more detail below, it is envisaged according to the present invention also to provide an apparatus, or device, for performing the method as described herein. Such a device, or system, may include apparatus or means for culturing the culture vessel and or any other culture steps according to the claimed method. Accordingly the various culture steps of the method, including the culture of the culture vessel containing the clinical sample culture, the culture of the microbial culture preparation in step (d) if required, or indeed also culture during the AST assay may be performed in the same or different culture systems or culture apparatus. The culture vessel containing the clinical sample culture may also be transferred to a different culture system/apparatus.

Thus for example, in one embodiment, the culture vessel (e.g. a first culture vessel) may be cultured in one system whilst the testing steps are being performed. If the AST assay is negative, inconclusive or incomplete, the culture vessel may then be transferred to a further, or separate culture system, e.g. to enable a conventional AST to be performed. For example, such a further or separate culture system may be a conventional culture cabinet, or a further automated microbial testing/detection system (e.g. diagnostic system).

By way of representative example, in one embodiment of the method, the clinical sample, collected from a test subject, is introduced into a culture vessel (this can be regarded as a first culture vessel). Before any culture takes place, ID tests to identify the microorganism are performed on an aliquot removed from the first culture vessel. The ID tests may be, for example, molecular ID tests to identify the microorganism (and optionally one or more genetic antimicrobial resistance markers in said microorganism), or may be performed by mass spectrometry (e.g. MALDI-TOF mass spectrometry, see e.g. Wahl et al. 2002. Anal Chem 15 74(24), 6191-9). Spectroscopic methods may also be used to determine the ID of a microorganism in a sample, and such methods are known in the art (see e.g. U.S. Pat. No. 8,652,800). However, in a preferred embodiment, the ID of a microorganism is determined using one or more molecular tests.

During this time the culture vessel is cultured. If a successful (positive) microbial ID result is obtained, a test aliquot is removed (according to step (b)), and subjected to steps (c)-(e). If the identification test is negative, the culture vessel containing the clinical sample culture may be subjected to further culturing, including in a separate system, or in the same system. During this time the culture vessel is cultured.

If it is found that an insufficient number of microbial cells is recovered from the test aliquot, the microbial culture preparation and/or the culture vessel containing the clinical sample culture may be subjected to further culturing, which may take place in the same system or in a separate system. After a period of culture of the microbial culture preparation, the concentration of microbial cells in the microbial culture preparation may be determined again to check that there are sufficient cells for the AST test. If there are, the AST test can proceed. Alternatively a further test aliquot then be removed from the clinical sample culture (after further culturing) and subjected to steps (c)-(d).

In a second embodiment, the method is performed as described above, but with a step of preculture before performing the identification tests.

In a third embodiment, the identification tests are performed on a fraction of an aliquot of the clinical sample culture which is removed from the culture vessel. During this time a further aliquot fraction or the remainder of the test aliquot is subjected to culture, as is the culture vessel from which the test aliquot is removed. This culture of the separate aliquot/aliquot fraction and culture vessel may take place in the same or different systems. If the identification test yields a positive result, the cultured further aliquot fraction/remaining aliquot is subjected to the AST test according to the method of the present invention, that is an aliquot is removed according to step (b) and (c) to (e) are performed. If the identification test is negative, the culture vessel containing the clinical sample is subjected to further culturing, e.g. in a separate system.

In a fourth embodiment, a portion is removed from a first culture vessel containing the clinical sample (whether before or after a period of preculture) and introduced into a second culture vessel containing culture medium. An aliquot is removed from the second culture vessel and subjected to identification tests. During this time the second culture vessel is cultured. If the identification test yields a positive result, a further aliquot (i.e. the test aliquot) is removed from the second culture vessel according to step (b) of the method of the invention and subjected to steps (c) to (e). If the identification test is negative, the second culture vessel containing the sample aliquot is subjected to further culturing. In a further embodiment, the first culture vessel may additionally or instead be subjected to further culturing, e.g. in a separate system.

In a further embodiment, the first, second, third and/or fourth representative embodiments described above may include continued culture of the culture vessel containing the clinical sample irrespective of whether a positive or negative identification result was obtained. In this way an additional result may be obtained from the clinical sample.

In an alternative embodiment the aforementioned representative embodiments may be performed by obtaining two clinical samples, and performing an identification method using a portion of the first clinical sample, whilst culturing a second clinical sample. Alternatively, a single clinical sample may be divided and separate portions may be used for ID an AST, e.g. to set up different cultures for ID and AST. Once an ID has been obtained for a microorganism in the first clinical sample (or first portion), a test aliquot may be removed from the second clinical sample (or second portion) (a clinical sample culture) before the culture reaches 0.5 McFarland units. The first clinical sample may be provided in a culture vessel comprising culture medium (e.g. a blood culture flask), or may not be provided in a culture vessel comprising culture medium (e.g. an EDTA blood tube), as in either event a test aliquot may be taken and subjected to an identification method as described herein. Preferably the second clinical sample is provided in a culture vessel containing culture medium, however, as discussed above a clinical sample may be not be provided in a culture medium, and thus the second clinical sample may be processed to recover the microbial cells contained therein, and a clinical sample culture may be established using microbial cells derived from the initial clinical sample whilst the ID of the microorganism is determined. As noted above, the adjustment of the concentration of microbial cells may be carried out in different ways.

In one preferred embodiment, if an insufficient number of microbial cells is recovered from the test aliquot, the microbial culture preparation may be cultured for a period of time, and a concentration determination step may be repeated at one or more time points until the cultured microbial culture preparation comprises a sufficient number of cells or cell concentration (e.g. a sufficiently high cell density) for an AST to be performed. Put another way, the step of adjusting the concentration of microbial cells prior to step (e) may encompass an incubation step, thereby increasing the number of microbial cells present in the microbial culture preparation to increase, without the need to take further test aliquots from the culture vessel containing the clinical sample culture.

In a further embodiment, if it is found that the microbial culture preparation comprises a cell density/number that is too high for an AST to be performed (i.e. if the concentration of the microbial culture preparation is too high), the microbial culture may be diluted with an appropriate buffer or culture medium in order to reduce the cell density to a suitable level. As discussed above, this dilution may take place as a separate step (i.e. a step of dilution of the microbial culture preparation (the AST inoculum)) or it may take place in the course of setting up (inoculating) the test microbial cultures for AST.

It will be seen therefore that once the concentration of microbial cells in the microbial culture preparation has been measured, the concentration may be adjusted (either by increasing or decreasing the concentration as mentioned above) prior to or during inoculating a series of test microbial cultures to ensure that an appropriate concentration of microbial cells is present in the test microbial cultures of step (e).

However, in a further embodiment, an AST assay may be performed using the microbial culture preparation obtained in step (d) (once the concentration of microbial cells is determined in step (e)), regardless of the concentration of microbial cells therein, e.g. using a non-standard concentration of microbial cells, and/or without any physical adjustment (as defined herein) to increase or decrease the concentration of microbial cells present in the microbial culture preparation.

The AST assay may be performed, and the results obtained therefrom may be adjusted by a factor depending on the concentration of microbial cells that were present in the initial microbial culture preparation and/or in the test microbial culture. In this way, the results obtained from an AST assay performed using a 'non-standard' microbial culture preparation may be correlated with results from AST assays performed using standard microbial cultures. Whilst this embodiment does not comprise a step of physically adjusting the concentration of microbial cells in the microbial culture preparation and/or in the test microbial cultures, it may nonetheless also be viewed as comprising an adjustment step, albeit a 'virtual' adjustment. Thus the term "adjusting the concentration" as used herein includes "adjusting for" the concentration, and does not require a physical adjustment.

Alternatively, in a further embodiment, an AST assay may be performed using the microbial culture preparation obtained in step (b) without first measuring the concentration of microbial cells in the microbial culture preparation. Rather, in this embodiment, the concentration of microbial cells is measured in the test microbial cultures before step (f).

The analysis of the microbial growth in the test microbial cultures in the AST test of steps (e) and (f) may take account of the microbial cell concentration in the AST test microbial cultures at the start of the incubation (Time=zero, T0) in the determination of the MIC value. In this way the microbial cell concentration may be "adjusted", if necessary.

Again, therefore, it can be seen that a virtual adjustment may be carried out, adjusting for the concentration of the microbial cells (as will be discussed in more detail below).

Thus, mathematical methods (e.g. algorithms) may be used to adjust a MIC value determined from the assessment of microbial growth in the test microbial cultures to obtain a standard MIC value.

Thus in the methods of the present invention it is not necessary to measure the concentration of microbial cells present in the initial culture vessel from which the test aliquot is taken (i.e. the clinical sample culture) or the test aliquot itself. In some embodiments, it is also not necessary to measure the concentration of microbial cells present in the microbial culture preparation, as long as the concentration of microbial cells is measured prior to step (f).

The concentration of microbial cells present in the microbial culture preparation may be measured, and if required, adjusted appropriately. Thus, the concentration of microbial cells may be adjusted to a suitable level for use in AST regardless of the concentration of microbial cells present in the clinical sample culture, and consequently in the initial test aliquot (e.g. by dilution or incubation as described above, or by a virtual adjustment). Alternatively, or additionally, the concentration of microbial cells present in the test microbial cultures may be measured (although if this is not measured, it may be calculated from the concentration of microbial cells in the microbial culture preparation). It is required, however, that the concentration of microbial cells present in the test microbial cultures is known.

Preferably, the concentration of microbial cells is measured by imaging, i.e. the concentration of microbial cells in the microbial culture preparation and/or a test microbial culture may be measured by imaging.

Thus, as discussed above, an advantage of the present invention is that it is not necessary to wait until a clinical sample culture reaches 0.5 McFarland units, or until a positive result in a culture test (microbial growth test) has been obtained, meaning that antimicrobial susceptibility may be initiated earlier, and thus be more rapidly determined. The methods of the present invention are thus performed before the clinical sample culture reaches 0.5 McFarland units, and preferably before a positive result is obtained or obtainable in a culture test.

The AST assay of steps (e) and (f) may, as described further below, be performed in any convenient or desired way. Accordingly, microbial growth may be assessed (or determined) in the presence of different antimicrobial agents (e.g. antibiotics) and/or amounts or concentrations of antimicrobial agent (e.g. antibiotic). Growth may be assessed directly or by assessing (determining) markers of growth.

Generally speaking, an AST assay is performed by monitoring the effect of an antimicrobial agent on microbial growth. A microbial culture (here the microbial culture preparation) is used to inoculate culture medium in a series of at least two culture vessels, each comprising a different concentration of an antimicrobial agent, and the microorganisms are cultured for a period of time. In this way, a series of at least two different concentrations of an antimicrobial agent is tested in order to determine the minimum inhibitory concentration (MIC) that is required in order to prevent microbial growth. The MIC value obtained thus provides an indication of whether a microorganism is resistant or susceptible to an individual antimicrobial agent.

In addition to inoculating at least two culture vessels comprising different concentrations of antimicrobial agents, an AST assay will have a positive control condition (culture medium that does not comprise an antimicrobial agent) in order to confirm that the microorganism is viable and is capable of growth in the growth medium provided, and a negative control condition (culture medium which has not been inoculated with a microbial culture and which does not comprise an antimicrobial agent) in order to confirm that the growth medium is not contaminated with a microorganism that is not obtained from the clinical sample. Thus, step (e) will include setting up suitable positive and negative control conditions, in addition to the at least two different growth conditions.

The positive control sample may be seen in some embodiments as providing a first concentration of an antimicrobial agent (i.e. a concentration of 0 M), and only a second condition comprising an antimicrobial agent may be set up. In such an embodiment, the growth in the positive control condition and the condition comprising an antimicrobial agent may be assessed in order to determine antimicrobial susceptibility. Thus "at least two different growth conditions, wherein . . . each antimicrobial agent is tested at two or more different concentrations" may be seen to encompass an embodiment in which an antimicrobial agent is added to only a single growth condition, and the positive control condition represents a second concentration of the antimicrobial agent.

In a preferred aspect, more than one (i.e. two or more) different antimicrobial agent is tested, thus providing two or more different MIC values, one for each different antimicrobial agent. The combination of different MIC values provides the antimicrobial susceptibility profile of a given microorganism, i.e. which of a panel of antimicrobial agents a microorganism is resistant to, and which of a panel of antimicrobial agents a microorganism is susceptible to. Separate positive and negative control conditions may be set up for each separate antimicrobial agent that is tested, if required, however a single positive and a single negative control condition will suffice where multiple different antimicrobial agents are tested.

Microbial growth may be assessed by determining the amount of microbial cell matter (that is microbial biomass) present in a sample (here, specifically, in the test microbial cultures set up for the AST test) particularly by assessing or determining this directly. In a preferred embodiment this is achieved by determining the amount of microbial biomass visually, and especially by imaging. In particular 2-D images may be obtained and assessed. Thus in a preferred embodiment the area of microbial biomass may be determined (more particularly the area of microbial biomass in the field of view under investigation, e.g. in an image).

Microbial growth may be assessed by determining the amount of microbial cell matter (that is microbial biomass) present in a sample (here, specifically, in the test microbial cultures set up for the AST test) particularly by assessing or determining this directly. In a preferred embodiment this is achieved by determining the amount of microbial biomass visually, and especially by imaging. In particular, 2-D images aligned perpendicularly to the optical axis (here termed xy-aligned) may be obtained and assessed. A specific area of the specimen is covered in a single xy-aligned image the size of which is dependent on the optical properties of the imaging apparatus. For each position in xy-space, one or more 2D images can be collected at different intervals along the optical or z axis. Thus, a series, or stack of 2D images can be generated, providing 3D information of a sample volume. An alternative method of extracting 3D information from a sample is that employed by Unisensor (see e.g. U.S. Pat. No. 8,780,181), where the optical axis is tilted with respect to the xy-plane, and the sample or detector is moved along either the x or y plane. Here, a series of images with an extension into z space, in addition to xy space, is acquired. Through a subsequent transformation of the image data, stacks of 2D images aligned perpendicularly to the xy plane can be achieved also with this method.

Once extracted, the 3D information inherent in the 2D image stacks can be utilized to estimate/infer/deduce the total cell mass present in the analysed volume. In a preferred embodiment, 2-D images may be generated from 3-D information by e.g. projections of z-stacks into one 2-D image. Analysis may then be performed using the resulting 2-D image. The area of microbial biomass may then be determined as the area of optical density indicating microbial biomass in the field of view under investigation, e.g. in the projected 2D image. Such a method is common practice in the art and may increase sensitivity, and algorithms for this for bright field images may be found in the publicly available software Cellprofiler from MIT, USA. Similar analysis may be performed for fluorescent images, and many alternative algorithms for this exist, e.g. in Cellprofiler, and also in most commercial image analysis systems.

In another embodiment, intensity variation in the z space stretching over each position in xy space is registered, indicating microbial mass in a specific position. Integrated over the entire xy space, this gives a measure of total microbial volume. Algorithms for this procedure also exist in commonly available image analysis software, e.g. in the freeware Cellprofiler.

More generally, microbial growth may be assessed by determining the amount and/or number and/or size of microorganisms and/or microbial colonies or aggregates. As will be discussed in more detail below, in certain preferred embodiments, microbial growth is assessed (determined) by imaging, or alternatively expressed, by visualising the microorganisms. Thus microbial cells, which may include aggregates or clumps (clusters) of cells, or microbial colonies, may be visualised or imaged as a means of determining (or assessing or monitoring) growth. This may include counting of cells or colonies, but is not limited to such methods and includes any means of visually assessing the amount of microbial growth by assessing (or determining) the size, area, shape, morphology and/or number of microbial cells, colonies or aggregates (the term "aggregate" includes any collection of cells in physical proximity e.g. a clump or cluster; this may include non-clonal clumps/clusters of cells which have aggregated or stuck together (e.g. neighbouring cells which have become aggregated) as well as clonal colonies). The parameter used to measure microbial growth may, but need not, vary according to the identity of the microbe and the antimicrobial agents used. Indeed, depending on the organism and the antimicrobial agents used, the morphology or growth pattern of the cells may be affected, and this may be altered or changed from the "normal" or "typical" morphology or growth pattern, e.g. in the absence of the antimicrobial agent. Whilst some AST growth monitoring methods may depend on detecting such changes, it is not essential according to the present invention to take such changes into account and the amount (e.g. area) of microbial growth or biomass may be determined irrespective of morphology and/or growth pattern. Thus the same growth monitoring method may be used regardless of the microbial cell and/or antimicrobial agents used. Methods for performing the AST assay are described further below.

Advantageously, the test aliquot removed from the clinical sample culture may be used directly in the methods of the present invention, i.e. steps (c)-(f) may be performed directly on the removed test aliquot. According to one embodiment of the present invention, there is no requirement for a further sub-culture step between removing the test aliquot and selectively isolating microbial cells therefrom. In particular there is no need for a sub-culture step in a further culture medium or culture vessel, or more particularly, there is no step of sub-culturing to obtain a pure culture prior to performing steps (c)-(f) of the present invention. This means that a more rapid AST assay may be performed.

Advantageously, a rapid AST assay is performed. Accordingly, in a preferred embodiment the AST assay of steps (e) and (f) may give a result in 8, 7, or 6 hours or less, for example in 4 or 5 hours or less.

The monitoring or assessing of microbial growth in the AST assay may take place by monitoring growth continuously or at intervals over a time period (e.g. up to 1, 2, 3, 4, 5, 6, 7 or 8 hours), or by comparing the amount of microbial cell matter at the time the AST growth culture (test microbial culture) is initiated (t0) with the amount of microbial cell matter at a later time point (e.g. at up to 1, 2, 3, 4, 5, 6, 7, or 8 hours), i.e. the growth that has taken place in the intervening time. Alternatively, the amount of microbial cell matter may be determined at two or more different time points (e.g. measuring the first time point after 1, 2, 3 or 4 hours, and measuring a second time point 1, 2, 3, 4, 5, 6 or 7 after the first time point, or 2, 3, 4, 5, 6, 7 or 8 hours after the initiation of culture) and the amount of growth may thereby be determined. In preferred embodiments, the degree of microbial growth may be determined at more than one time point, i.e. at at least two time points.

In another embodiment, growth is assessed in a test microbial culture grown in the presence of an antimicrobial agent with a test microbial culture grown in absence of antibiotics (e.g. a positive control) at only one time point, e.g. at 1, 2, 3, 4, 5, 6, 7 or 8 hours. Monitoring growth at a time point (or two or more time points) after the initiation of the AST growth culture may advantageously allow a more accurate result to be achieved by avoiding measuring growth during the lag phase of microbial growth, as any differences between microbial growth under different conditions during this period of time will be small and difficult to detect. A first measurement may be taken according this method after 30 minutes or 1, 2, 3 or 4 hours, and a second measurement may be taken 1, 2, 3, 4, 5, 6, 7 or 8 hours after the first time point).

It will be apparent, however, that for certain microorganisms, e.g. certain anaerobes, mycobacteria or fungi, microbial growth may be less rapid, and thus an AST assay may need to be performed for a longer period of time. Thus, according to certain embodiments of the present invention, it may be necessary or desirable to perform the AST assay by measuring microbial growth for 8, 9, 10, 11 or 12 hours or more, e.g. 12, 18 or 24 hours. Suitable measurements at one or more time points may be taken accordingly.

In a preferred embodiment, growth may be measured in at least two growth conditions (e.g. each growth condition), relative to the initial number (amount or concentration) of microbial cells in each growth condition.

The method of the invention may be used determining the antimicrobial susceptibility of any microorganism. Generally speaking clinically relevant microorganisms are concerned. As used herein, the term microorganism encompasses any organism which may fall under the category of "microorganism". Although not necessarily so, microorganisms may be unicellular, or may have a unicellular life stage. The microorganism may be prokaryotic or eukaryotic and generally will include bacteria, archaea, fungi, algae, and protists, including notably protozoa. Of particular interests are bacteria, which may be Gram-positive or Gram-negative or Gram-indeterminate or Gram-non-responsive, and fungi.

Particularly, clinically relevant genera of bacteria include *Staphylococcus* (including Coagulase-negative *Staphylococcus*), *Clostridium*, *Escherichia*, *Salmonella*, *Pseudomonas*, *Propionibacterium*, *Bacillus*, *Lactobacillus*, *Legionella*, *Mycobacterium*, *Micrococcus*, *Fusobacterium*, *Moraxella*, *Proteus*, *Escherichia*, *Klebsiella*, *Acinetobacter*, *Burkholderia*, *Entercoccus*, *Enterobacter*, *Citrobacter*, *Haemophilus*, *Neisseria*, *Serratia*, *Streptococcus* (including Alpha-hemolytic and Beta-hemolytic *Streptococci*), *Bacteriodes*, *Yersinia*, and *Stenotrophomas*, and indeed any other enteric or coliform bacteria. Beta-hemolytic *Streptococci* would include Group A, Group B, Group C, Group D, Group E, Group F, Group G and Group H *Streptococci*.

Non-limiting examples of Gram-positive bacteria include *Staphylococcus aureus*, *Staphylococcus haemolyticus*, *Staphylococcus epidermidis*, *Staphylococcus saprophyticus*, *Staphylococcus lugdunensis*, *Staphylococcus schleiferei*, *Staphylococcus caprae*, *Staphylococcus pneumoniae*, *Staphylococcus agalactiae* *Staphylococcus pyogenes*, *Staphylococcus salivarius*, *Staphylococcus sanguinis*, *Staphylococcus anginosus*, *Streptococcus pneumoniae*, *Streptococcus pyogenes*, *Streptococcus mitis*, *Streptococcus agalactiae*, *Streptococcus anginosus*, *Streptococcus equinus*, *Streptococcus bovis*, *Clostridium perfringens*, *Enterococcus faecalis*, and *Enterococcus faecium*. Non-limiting examples of Gram-negative bacteria include *Escherichia coli*, *Salmonella bongori*, *Salmonella enterica*, *Citrobacter koseri*, *Citrobacter freundii*, *Klebsiella pneumoniae*, *Klebsiella oxytoca*, *Pseudomonas aeruginosa*, *Haemophilus influenzae*, *Neisseria meningitidis*, *Enterobacter cloacae*,

*Enterobacter aerogenes, Serratia marcescens, Stenotrophomonas maltophilia, Morganella morganii, Bacteriodes fragilis, Acinetobacter baumannii* and *Proteus mirabilis*.

Clinically relevant fungi may include yeasts, particularly of the genus *Candida*, and fungi in the genera *Aspergillus, Fusarium, Penicilium, Pneumocystis, Cryptococcus, Coccidiodes, Malassezia, Trichosporon, Acremonium, Rhizopus, Mucor* and *Absidia*. Of particular interest are *Candida* and *Aspergillus*. Non-limiting examples of fungi include *Aspergillus fumigatus, Candida albicans, Candida tropicalis, Candida glabrata, Candida dubliensis, Candida parapsilosis*, and *Candida krusei*.

The term "detecting" refers broadly to any means of determining the presence or absence of a microorganism. Thus "detecting" may include determining, assessing or measuring in any way or form whether or not a microorganism is present—it may include qualitative, quantitative or semi-quantitative determinations.

The term "characterising" means broadly any means of determining information about the nature and/or properties of the microorganism, and includes particularly identifying the microorganism. More particularly the microorganism may be identified in terms at least of its genus, and preferably its species. In some cases even identification at the level of strain may be possible. The method of the invention also allows the microorganism to be characterised in terms of determining whether or not it is susceptible, or is expected to be susceptible, to given antimicrobial agents, or whether it demonstrates resistance or is expected to be resistant to any antimicrobial agents e.g. determining its antimicrobial susceptibility profile. This may be done by testing for the presence of molecular resistance markers, namely genetic variants or particular genetic sequences which are associated with, or indicative of resistance to one or antimicrobial agents, or classes of antimicrobial agent. Such molecular tests of course do not determine conclusively that the microorganism is susceptible and this is done by the AST assay of steps (e) and (f) in which the effect of the antimicrobial agent on the growth of the microorganism is tested directly.

The term "lysing" means breaking down of a cell. In particular, the cell is broken down to release cell contents, including particularly nucleic acid, This may be achieved by any means, as vast number of which are known in the art, for example by viral, enzymatic, mechanical, electrical, chemical, heat, cold or osmotic mechanisms that compromise its integrity leading to the partial or full release of cellular components into surrounding solution.

The term "selectively lysing" or "selective lysis" means lysing of a particular subset of the cells present in a sample. For instance, it may be desirable to selectively lyse only the non-microbial cells, or more particularly the cells which derive from the subject under test (e.g. mammalian cells) that are present in a clinical sample, without substantially lysing the prokaryotic or microbial cells present in a clinical sample. In addition, the present invention requires that the microbial cells obtained from the sample are able to grow and reproduce (growth is required in order to determine antimicrobial susceptibility), and thus it is desirable that the ability of the microbial cells to grow and/or reproduce (viability) is not affected by the selective lysis of the non-microbial or test subject-derived cells that are present in a sample. Suitable conditions for selective lysis are known in the art and discussed in more detail below.

The term "viable" defines microbial cells which are able to grow and/or reproduce. The term "viability" refers to the ability of microbial cells to grow and/or reproduce. It is of particular importance in the methods of the present invention that the viability of the microbial cells present in a sample is not substantially reduced as a result of the selective lysis methods used to lyse the non-microbial cells in a sample. Viability may be quantified as a measure of the percentage of cells which are capable of growth and/or reproduction. Preferably all (i.e. 100%), or substantially all of the microbial cells recovered from a sample may be viable following any such treatment, and it is preferred that at least 99%, 98%, 97%, 96%, 95%, 94% 93%, 92%, 91% or 90% or microbial cells recovered from a sample are viable following the selective lysis step. However, it is contemplated that antibiotic susceptibility may still be assessed in the event that at least 80%, 70%, 60% or 50% of the recovered microbial cells are viable. However, the cells recovered from the sample may represent only a fraction of the cells recovered, and the present methods may be performed if at least 10%, 9%, 8%, 7%, 6%, 5%, 4%, 3%, 2% or 1% or less of the total microbial cells present in the clinical sample are viable.

Viability may be assessed by measuring the growth rate of a microbial culture that has been processed according to the present method and comparing to a microbial culture that has not been processed. Processing a clinical sample to recover microbial cells may have an effect on the rate of microbial growth, however it is preferred that this will not have any significant effect on the rate of microbial growth. However, microbial cultures having at least 90%, 80%, 70%, 60%, 50%, 40%, 30%, 20% or 10% the growth rate of a culture that has not been processed in this way may still be used as a microbial culture preparation for use in determining antibiotic susceptibility of a microorganism.

The clinical sample may be any clinical sample that may be obtained from a test subject, which generally will be a human patient but may be any human or animal, generally mammalian, subject. It may thus be any sample of body tissue, cells or fluid, or any sample derived from the body, e.g. a swab, washing, aspirate or rinsate etc. Suitable clinical samples include, but are not limited to, blood, serum, plasma, blood fractions, joint fluid, urine, semen, saliva, faeces, cerebrospinal fluid, gastric contents, vaginal secretions, mucus, a tissue biopsy sample, tissue homogenates, bone marrow aspirates, bone homogenates, sputum, aspirates, wound exudate, swabs and swab rinsates e.g. a nasopharyngeal swab, other bodily fluids and the like. In a preferred embodiment, the clinical sample is sample is blood or a blood-derived sample, e.g. serum or plasma or a blood fraction.

The microorganism may be any microorganism (e.g. any bacterial or fungal microorganism), in particular any pathogenic microorganism or any microorganism causing an infection in the body, and thus the method may be used in the context of detecting or diagnosing a microbial infection in or on any part of the body of a test subject (i.e. any microbial infection) and the nature of the clinical sample may be determined accordingly, e.g. according to the presentation of symptoms of the infection or suspected infection, or the general clinical condition of the subject. Although any microbial infection is encompassed, the method of the invention has particular utility in the detection or diagnosis of sepsis (or more generally management of sepsis), or where sepsis is suspected. Thus the clinical sample may be from a subject having, or suspected of having, or at risk of, sepsis. In such a case the sample will generally be blood or a blood-derived sample. Typically the sample will be blood.

The clinical sample is introduced to a culture vessel comprising culture medium. This is a standard step which may be carried out according to standard procedures well known in the art and widely described in the literature.

A culture vessel can include any vessel or container suitable for the culture of microbial cells, e.g. a plate, well, tube, bottle, flask etc. Conveniently, where the sample is blood or a blood derived sample the culture vessel is a blood culture flask, for example a BacT/ALERT (Biomerieux) blood culture flask, a Bactec blood culture flask (Becton Dickinson) or VersaTrek blood culture flask (Thermo Fisher), or indeed any tube, flask or bottle known for the sampling of blood, particularly for the purpose of culture to detect microorganisms.

Conveniently the culture vessel may be provided with the culture medium already contained therein. However, the culture medium may be separately provided and introduced into the culture vessel, either prior to, simultaneously with, or after the clinical sample has been added.

Certain commercially available culture vessels (e.g. blood culture flasks) are provided with resin beads, which resin neutralise the effect of any antimicrobial agents which are present in the clinical sample (i.e. which had been administered to the subject under test) in order to facilitate the growth of the microbial cells in culture. In a preferred embodiment, the test aliquot may be filtered in order to remove any resins that may have been removed from the culture vessel when the test aliquot was obtained. Preferably, this step of filtration will utilise a filter having a pore size which does not substantially remove any cellular matter from the test aliquot, but which can remove the resin particles, e.g. at least 100, 200 or 300 μm but could be up to 1000 μm.

The culture medium may be any suitable medium and may be selected according to the nature of the clinical sample and/or the suspected microorganism, and/or clinical condition of the subject etc. Many different microbial culture media suitable for such use are known. Typically the culture medium may contain sufficient nutrients to promote rapid growth of microorganisms, as is known in the art. In many cases appropriate media are complex growth media comprising media such as Muller-Hinton (MH) media, MH-fastidious (MHF), Muller-Hinton supplemented with lysed horse blood, Lysogeny broth (LB), 2× YT Media, tryptic soy broth, Columbia broth, brain heart infusion broth, Brucella broth, as well as general purpose growth media known in the art, and may include the addition of particular growth factors or supplements. The culture may or may not be agitated. Culture media are available in various forms, including liquid, solid, and suspensions etc. and any of these may be used, but conveniently the medium will be a liquid medium. Where the culture vessel is a ready to use blood culture flask, as described above, these vessels may contain specified media especially modified to allow a wide range of microorganisms to grow. Typically medium supplied in a blood culture flask by a manufacturer will contain an agent or additive to neutralise the presence of any antibiotics present in a clinical sample taken from a test subject. Flasks containing or not containing such neutralising agents may be used, and neutralising agents may be added to the culture vessel if desired.

As noted above, a first test aliquot may be removed from the clinical sample culture at any time before the test culture reaches 0.5 McFarland units, once an ID has been obtained. Generally speaking there will be a period of culture of the clinical sample in the culture vessel to allow microorganisms present in the clinical sample to grow (i.e. multiply), before the test aliquot is removed, microbial cells are isolated and the AST assay is performed. This period of culture may vary depending on the details of the specific method being performed, test subject, microorganism etc. However, it is advantageous that this is as short as possible. In certain embodiments, the clinical sample culture (or more particularly an aliquot removed therefrom) is subjected to microbial detection and/or characterisation tests to identify any microorganism that is present in the clinical sample (e.g. molecular identification tests) prior to the removal of the test aliquot in step (b) of the method and during the identification tests the clinical sample culture is kept in culture. This may accordingly be for a period of e.g. up to 1, 2, 3, 4, 5, 6, 7, 8 or 9 hours e.g. 4 to 7 hours all 4 to 6 hours. It is generally advantageous to wait for an identification result, in order that the microbial identification may inform the AST test (i.e. the antimicrobial agents used in the AST test may be selected depending upon the result of microbial identification). However, this is not essential and it is possible, depending on the sample that the test aliquot in step (b) may be removed very shortly after setting up the clinical sample culture e.g. immediately or substantially immediately after the sample is contacted with the culture medium in the culture vessel (for example after mixing the sample and medium). This may for example be within 10, 15, 20 or 30 minutes of introducing the sample to the culture vessel, or it may be longer, e.g. within 1, 2, 3 or 4 hours, depending on the clinical situation.

The length of any culturing of the clinical sample culture that is performed may depend on the nature of the sample, and the suspected infection, clinical status of the subject etc. For example, in the case of a urine sample, a high number of microbial cells are expected to be present in the sample and hence a culture step, or a prolonged culture step, may not be required, However, in the case of a blood sample for example, the number of cells is generally expected to be less and a culture step may be advantageous or necessary to increase the number of microbial cells available, before the test aliquot is removed in step (b).

Culturing (of the clinical sample culture, or any other culture e.g. test microbial cultures or a microbial culture preparation) generally involves incubating the culture vessel under conditions conducive to, or suitable for, microbial growth e.g. at a particular temperature (for example, at a temperature from 20 to 40° C., or 25 to 40° C. e.g. 25 to 37° C., or 30 to 35° C. Depending on the nature of the vessel, medium, suspected microorganism, clinical condition etc., the vessel may be agitated or rotated, shaken etc.

Culturing of the clinical sample culture can take place for any suitable or desired time period, but in order to speed up the method it will preferably be for a short time period of less than 8 or less than 6 hours. For example culture may take place for up to 1, 2, 3, 4, 5 or 6 hours prior to the removal of the test aliquot in step (b). Alternatively culturing can take place for less than 1 hour. Culturing can also take place for more than 6 hours, for example for 7, 8 or 9 hours, or more than 9 hours, for example up to 10, or 12 hours, or even longer, but in the interests of providing a rapid method it is generally kept to a minimum, and short culture periods of up to 6, or more particularly up to 4 or 3 hours are preferred. As noted above, culture takes place for a period shorter than is required to see a positive culture result.

Removal of the test aliquot in step (b) may take place by any convenient means, depending on the nature of the culture vessel and how it is incubated. For example in the case of a blood culture flask an aliquot may simply be withdrawn using a needle and syringe. According to normal clinical and microbiological practice steps may be taken to avoid or limit contamination, e.g. this may be done under aseptic conditions.

In one convenient embodiment, the means for removal of the test aliquot (e.g. the needle, and optionally the syringe), may be provided in single-use form, i.e. as a consumable. In other words it may be disposable and not re-used.

The methods of the present invention require the selective isolation, or enrichment, of microbial cells in a sample. "Enrichment" means any method of increasing the concentration of microbial cells within a sample, or removing or otherwise reducing the concentration of any non-microbial cells from the sample. In the present context, enrichment may comprise both the removal of cells which derive from the subject under test (e.g. mammalian cells) from a sample, and recovery of the microbial cells therefrom. In other words, the present invention requires the separation of microbial cells from the clinical sample culture (or more particularly the test aliquot removed therefrom), so that they may be used in an AST assay to determine antimicrobial susceptibility.

Suitable methods for enriching a sample for microbial cells may include lysing any non-microbial cells present in the aliquot, and/or selectively recovering microbial cells from the aliquot (i.e. positive or negative selection of microbial cells from the aliquot). Methods for doing this are known in the art.

Methods for selectively lysing non-microbial cells for selectively enriching microorganisms in a sample, which are not dependent on knowing the identity of the microorganisms, are described for example in US 2013/0171615, US 2012/0231446, US 2010/0184210, U.S. Pat. Nos. 7,893,251 and 8,481,265, and methods for selectively removing eukaryotic cells from a sample are described in US 2005/0202487.

The removal from the test aliquot of the clinical sample culture of any cells which derive from the subject under test (i.e. any non-microbial eukaryotic cells) may be done under any conditions which lyse non-microbial eukaryotic cells, preferably mammalian cells, but which do not lyse microbial cells, and preferably which maintain the viability of the microbial cells. For example, an appropriate lysis reagent, e.g. a lysis buffer, may be added to the test aliquot.

Preferred lysis buffers selectively lyse undesired cells (e.g. non-microbial cells/cells derived from the subject under test) that may be present in the test aliquot. The selective lysis of non-microbial cells allows the microbial cells to be separated from other components that may be present in the sample, for subsequent antimicrobial susceptibility testing. The lysis buffer thus is one that is capable of selectively lysing cells (e.g. mammalian cells) e.g. by solubilising cell membranes. The lysis buffer may comprise one or more detergents, one or more chaotropes, one or more enzymes, or any combination thereof.

Useful detergents may include one or more non-denaturing lytic detergents, such as Triton X100-R, Triton X-114, NP-40, Genapol C-100, Genapol X-100, Igepal CA 630, Aslasolve 200, Brij 96/97, CHAPS, octyl β-D-glucopyranoside, saponin and nonaethylene glycol monododecyl ether (C12E9, polidocenol). Optionally, denaturing lytic detergents can be included, such as sodium dodecyl sulphate (SDS), N-laurylsarcosine, dodium deoxycholate, bile salts, hexadecyltrimethylammonium bromide, SB3-10, SB3-12, amidosulphobetaine-14 and C7BzO. Optionally solubilisers can also be included, such as Brij 98, Brij 58, Brij 35, Tween 80, Tween 20, Pluronic L64, Pluronic P84, non-detergent sulphobetaines (NDSB 201), aphipols (PMAL-C8), and methyl-β-cyclodextrin. In one embodiment polyoxyethylene detergent detergents may be preferred. The polyoxyethylene detergent can comprise the structure $C_{12-18}/E_{9-10}$, wherein C12-18 denotes a carbon chain length of 12 to 18 carbon atoms and E9-10 denotes from 9 to 10 oxyethylene hydrophilic head groups. For example, the polyoxyethylene detergent can be selected from the group consisting of Brij 97, Brij 96V, Genapol C-100, Genapol X-100, nonaethylene glycol monododecyl ether (polidocanol), or a combination thereof and ethylene-diaminetetraacetic acid (EDTA).

The lysis solution may also comprise one or more enzymes. Enzymes that can be used in the lysis solutions include, without limitation, enzymes that digest nucleic acids and other membrane-fouling materials (e.g. proteinase XXIII, DNase, neuraminidase, polysaccharide, Glucanex and Pectinex, Proteinase K, Micrococcal nuclease, pepsin or trypsin).

Suitable chaotropes or chaotropic agents may include urea, guanidinium hydrochloride, butanol, ethanol, lithium perchlorate, lithium acetate, phenol, propanol or thiourea.

In another embodiment, one or more additional agents can be used, including for example reducing agents such as 2-mercaptoethanol or dithriothreitol (DTT), stabilising agents such as magnesium, pyruvate and humectants, and/or chelating agents such as ethylenediaminetetraacetic acid (EDTA). The lysis solution can be buffered at any pH that is suitable to lyse the desired cells, and will depend on multiple factors, including without limitation, the type of sample, the cells to be lysed, and the detergent used. In some embodiments, the pH can be in a range from 2-13, e.g. 6-13, 8-13, or 10-13. Suitable pH buffers include any buffer capable of maintaining a pH in the desired range, e.g. about 0.05 M to about 1.0 M CAPS.

Additionally, the lysis buffer may comprise any suitable salts, including NaCl, KCl, $MgCl_2$, $Na_2HPO_4$, $NaH_2PO_4$ which might aid lysis, or the subsequent handling of the microbial cells. Salts may, if present, be present at any suitable concentration, e.g. at least 0.01M, 0.02M, 0.05M, 0.1M, 0.2M, 0.5M, 1M, 2M or 5M, depending on the factors such as the volume of buffer and sample used.

Procedures and reagents for lysis of non-microbial cells and the isolation of microbial cells from mixtures comprising non-microbial cells are commercially available, for example from Molzym or Biocartis. Other lysis conditions and methods are disclosed, for instance, in Sullivan et al. 1975, J Clin Microbiol 1, 30-36; Zierdt et al. 1977 J Clin Microbiol 5, 46-50.

Alternatively, rather than selectively removing non-microbial cells, microbial cells may positively be selected from the test aliquot. For example if the identity of the microorganism is known microbial cells may be selected by binding to immobilised or immobilised double ligands (affinity binding partners) capable of specifically or selectively binding to the microbial cells.

Following the removal (e.g. lysis) of the non-microbial cells from a test aliquot, the microbial cells may be recovered from the resulting mixture (e.g. lysate). Although in one embodiment the separation and recovery steps may be seen as one and the same (e.g. the method may be performed in such a way that microbial cells are selectively separated from the test aliquot, or recovery is performed by lysis of non-microbial cells), in a preferred embodiment microbial cells are recovered from the lysate as a separate step, i.e. they are physically recovered from the sample after the lysis step. This may be done in any convenient way, e.g. by filtration or centrifugation.

Advantageously recovery may be performed using filtration using a filter comprising a suitable pore size to capture any microbial cells whilst allowing the flow-through of any other components of the sample e.g. culture medium and/or lysed mammalian cell debris and fragments. Following filtration the microbial cells recovered on the filter may optionally be washed using any suitable wash buffer comprising one or more components as defined above for the lysis buffer, e.g. a detergent. Alternatively, recovery of the microbial cells following the removal of non-microbial cells may be performed by centrifugation i.e. to sediment the intact microbial cells from a suspension to form a pellet. The resulting supernatant may then be discarded. The microbial pellet may be resuspended in a suitable wash buffer, as defined above, and centrifuged a further time to form a pellet. Alternatively microbial cells may be retrieved by using the entire filter, e.g. either by adding culture media to the filter for a continued pre-culture before AST.

Following recovery of the microbial cells from the sample the recovered cells are resuspended in a culture medium, suitable for microbial cell growth to obtain a microbial culture preparation.

In a preferred embodiment of the present invention, the microbial cells are recovered from the sample by filtration, and are resuspended from the filter directly using culture medium. The cells may be resuspended from the filter by repeated pipetting to resuspend the cells from the surface of the filter. In a preferred embodiment of the invention the culture medium may be back-flushed through the filter (i.e. in the opposite direction to which the filtrate was filtered) in order to resuspend the microbial cells. In an alternative embodiment, wherein the microbial cells are recovered by centrifugation, the microbial culture may be obtained by resuspending the pellet in culture medium. An alternative format is to recover the bacterial by using hollow fibres such as in U.S. Pat. No. 7,547,526.

The culture medium which is used to prepare the microbial culture preparation (i.e. in which the microbial cells are suspended) is generally speaking a culture medium which is approved or recognised for use in AST tests. Preferably, the culture medium is a liquid medium. Accordingly in one embodiment it is a Muller-Hinton (MH) medium or a Muller-Hinton Fastidious (MHF) medium or cation-adjusted Mueller Hinton medium. For non-standard AST any other medium commonly known may be used with the invention. MIC values obtained by performing an AST assay using a 'non-standard' culture medium may be adjusted (correlated) to give standard AST results.

Once the microbial cells have been recovered following removal of the non-microbial cells from the sample, and a microbial culture preparation is obtained, the concentration of microbial cells present in the microbial culture preparation is measured before the AST assay is performed. The determination of the concentration of microbial cells in the microbial culture may be performed by any convenient method, e.g. by counting (e.g. by haemocytometry or flow cytometry), turbimetric methods or by imaging, or by any of the methods described herein for assessing the amount of biomass in a sample.

The concentration determination step may be performed directly on the microbial culture preparation, or on a portion (e.g. a sample or aliquot or fraction) removed therefrom. Alternatively, the concentration may be determined after the microbial culture preparation has been used to inoculate the test microbial cultures, i.e. directly in the test microbial cultures.

It is required that the initial concentration of microbial cells present in the test microbial cultures is known. This may be achieved, for instance, by adjusting the concentration of microbial cells in the microbial culture preparation once it has been measured. Thus, the concentration of microbial cells in the microbial culture preparation may optionally, or if necessary, be adjusted, e.g. to fall within a range suitable for use in an AST assay. This adjustment may not be required in every instance, i.e. the microbial culture preparation obtained from the recovered microbial cells may be used directly to inoculate the series of test microbial cultures that are set up in step (e) (i.e. the microbial culture may be used directly, i.e. without any further adjustment). As noted above, a pre-determined or desired concentration of microbial cells may be present in the (optionally adjusted) microbial culture preparation which is used to set up the test microbial cultures for the AST. Alternatively, and as discussed above, this may be achieved by measuring the concentration of microbial cells present in the test microbial cultures directly, i.e. during step (e) of the methods of the present invention.

AST assays typically utilise microbial cultures having set (or standard or standardised) cell densities or microbial concentrations in order to allow results obtained from one sample or in one location to be compared with those obtained elsewhere, as the response of microorganisms to antimicrobial agents is known to vary with the concentration of microorganisms in a sample, as well as the type and concentration of the antimicrobial agent itself. Factors influencing clinical outcomes such as the dosage of an antimicrobial agent and the treatment regime prescribed to a patient are based on results obtained from AST assays performed according to set standard criteria.

The results obtained in an AST assay performed using a 'non-standard' (or "non-standardised") microbial culture (the antimicrobial susceptibility profile of a microorganism, or a set of MIC values) may differ from the results obtained in an AST assay performed according to standard criteria, e.g. using a 'standard' microbial culture. However, the degree to which a MIC value obtained using a non-standard microbial culture varies from a MIC value obtained using a standard microbial culture may be determined, if the concentration of microbial cells in the microbial culture preparation used to inoculate the AST test cultures is known. It is thereby possible to calculate a theoretical 'standard' MIC value from an MIC value obtained using a non-standard microbial culture.

The degree to which the MIC value obtained using a non-standard microbial culture varies from a 'standard' MIC value may vary depending on the nature of the microorganism and the antimicrobial agent, and can be determined separately, e.g. for each different antimicrobial agent that is tested and for microbial cultures comprising different concentrations of microbial cells.

The present invention thus provides a method to determine the antimicrobial susceptibility profile of a microorganism using a microbial culture preparation comprising a non-standard concentration of microbial cells, wherein the concentration of microbial cells in the test microbial cultures is measured before the AST assay is performed (i.e. the concentration of microbial cells in the microbial culture preparation is determined between steps (d) and (e), or the concentration of microbial cells is determined in the test microbial cultures during or after step (e) but prior to step (f), and the MIC value obtained in the AST assay may be adjusted based on the concentration of microbial cells in the test microbial cultures to give a standard MIC value.

Whilst said method may be performed using a microbial culture preparation comprising any concentration of microbial cells, for instance $10\text{-}10^9$ CFU/ml, it is essential that the concentration of microorganisms that is present in the test microbial cultures is known before the results of the AST assay are collected.

The inoculum used to set up an AST test assay in the methods of the prior art typically is approximately 0.5 McFarland units. As mentioned above, this corresponds to approximately $10^8$ CFU/ml. This is typically diluted in a 1:200 dilution to provide test microbial cultures comprising approximately $5\times10^5$ CFU/ml. However, whilst the methods of the present invention may use these standard values, it is possible in the methods of the present invention for the inoculum (the microbial culture preparation) and/or the test microbial cultures to comprise any defined or pre-determined concentration of microbial cells, provided the concentration of microbial cells in the test microbial cultures that are used to obtain an AST value is known.

The concentration of microbial cells in the microbial culture preparation may therefore be any desired or pre-determined concentration that is suitable for setting up a microbial test culture in an AST method. It may therefore be at least 10, $10^2$, $10^3$, $10^4$, $10^5$, $10^6$, $10^7$, $10^8$ or $10^9$ CFU/ml. Preferably the concentration of microbial cells in the microbial culture preparation will be $10\text{-}10^9$, $10^2\text{-}10^9$, $10^3\text{-}10^9$, $10^4\text{-}10^9$ CFU/ml, $10^5\text{-}10^9$ CFU/ml, $10^6\text{-}10^9$ CFU/ml, $10^7\text{-}10^9$ CFU/ml.

Such a method has particular utility if the concentration of microbial cells in the microbial culture preparation is below the standard concentration, as it may bypass the need to incubate said microbial culture preparation for a period of time in order to allow the concentration of microbial cells in the microbial culture preparation to increase.

The above may be viewed as a method to determine the 'standard' antimicrobial susceptibility profile of a microorganism by adjusting the MIC values obtained by performing an AST assay using a non-standard microbial culture. Viewed another way, the above provides a theoretical way to adjust the concentration of microbial cells that is used to inoculate the test cultures used in an AST assay, thereby to calculate the antimicrobial susceptibility of a microorganism.

Whilst it is possible to use a non-standard microbial culture to inoculate the test cultures used in the present invention, in an alternative embodiment the present invention provides methods to physically adjust the concentration of microbial cells present in a microbial culture preparation and/or test microbial cultures so that the concentration of microbial cells in the test microbial cultures corresponds to a standard or standardised concentration, (e.g. $5\times10^5$ CFU/ml) in order that a standard AST assay may be performed.

The microbial culture preparation is used to inoculate the test microbial cultures. As discussed above, the microbial culture preparation may be added to culture medium comprising, i.e. the microbial culture preparation may be diluted at this stage. Thus, the test microbial cultures may be adjusted at this point to comprise any desired or pre-determined concentration. Thus, the test microbial cultures will comprise an initial concentration of microbial cells of at least 10, $10^1$, $10^2$, $10^3$, $10^4$, $10^5$, $10^6$, $10^7$, $10^8$ or $10^9$ CFU/ml, preferably $10^2\text{-}10^8$, $10^3\text{-}10^7$ or $10^4\text{-}10^6$ CFU/ml.

In one embodiment, wherein the microbial culture preparation comprises a microbial concentration that is too high to be used in an AST assay, the microbial culture may be diluted using an appropriate buffer or culture medium (e.g. liquid culture medium) in order to reduce the cell density to a suitable level for an AST to be performed. Preferably the dilution is performed using the culture medium which is to be used to perform the AST assay. In one embodiment this may be performed using Muller Hinton (MH) broth.

In an alternative embodiment, wherein the microbial culture preparation comprises a microbial concentration that is too low to be used in an AST assay, the microbial culture preparation may be cultured for a period of time in order to allow the microorganisms present in the culture to grow and increase in number. The concentration of microbial cells present in the culture may be monitored either continuously or at a series of individual time points until the concentration of microorganisms in the microbial culture reaches a sufficiently high cell density that an AST assay may be performed (i.e. that steps (e) and (f) may be performed). Growth of the microbial culture at this stage may be monitored by any of the methods described herein for monitoring growth in the AST assay itself, e.g. imaging or counting of cells or colonies.

Thus, in one embodiment the present invention utilises an inoculum (microbial culture preparation) having a standard microbial concentrations (e.g. 0.5 McFarland units or $10^8$ CFU/ml) in order to inoculate the test cultures used in an AST assay. The concentration of microbial cells present in the microbial culture preparation obtained in step (d) may optionally, or if necessary be adjusted, that is increased or decreased depending on the number of cells present in the culture, in order to obtain a standard microbial culture. Alternatively, the concentration of microbial cells present in the microbial culture preparation may lie within a standard range, without the need for an adjustment step to be performed. Regardless, the concentration of microbial cells present in the microbial culture preparation obtained in step (d) may be measured, and may be adjusted as and if required to obtain a standard microbial culture. Alternatively, the microbial culture preparation may be used without adjustment and the concentration of microbial cells in the test microbial cultures may be adjusted (e.g. by selecting an appropriate dilution factor for setting up the test culture or an appropriate volume.

It is noted however that what constitutes a 'standard' culture preparation may vary depending on the identity of the microorganism, i.e. the concentration of microbial cells present in the culture preparation may depend on the identity of the microorganism. Preferably the concentration of microbial cells in the microbial culture preparation will be $10\text{-}10^9$ $10^2\text{-}10^9$, $10^3\text{-}10^9$, $10^4\text{-}10^9$ CFU/ml, $10^5\text{-}10^9$ CFU/ml, $10^6\text{-}10^9$ CFU/ml, $10^7\text{-}10^9$ CFU/ml. Recognised and pre-scribed conditions for AST assaying exist, and may be followed in order that readily comparable results may be obtained which are comparable to, or may be compared with, tests performed in other laboratories. This may involve for example the use of a prescribed medium and culture conditions. Thus, the isolated (separated or enriched) microorganisms may be transferred into a suitable medium for microbial culture, for example Mueller-Hinton medium (MH-media), prior to the commencement of the antimicrobial susceptibility test. In certain embodiments, medium for microbial culture may be a liquid medium, i.e. the culture medium may be a liquid. Microorganisms may be grown in the presence of a variety of antimicrobial agents to determine their susceptibility to a given antimicrobial agent. The antimicrobial agents may be selected based on the identity of the microorganism, if known, and preferably also on the nature of any genetic antimicrobial resistance markers identified within the microorganism. The antimicrobial agents, and the amounts to be used, may also be selected according to current clinical practice, e.g. according to which antimicrobial agents are currently used in practice to treat the identified microorganism, in order that the susceptibility of the microorganism to the currently accepted or recognised antimicrobial treatment of choice can be assessed. Thus antimicrobial agents can be selected based on those known to be effective against the identified microorganism, or those currently used in practice to treat the microorganism, and excluding any agents to which resistance might be expected based on the presence of resistance markers, or such agents might be included and the amounts used might be selected to allow the determination of an amount or concentration of the antimicrobial agent that may be effective, despite the presence of the resistance marker. Antimicrobial agents are added to culture medium to a range of final concentrations or amounts. In one embodiment of the present invention a dilution of the antimicrobial agent may be performed. In a preferred format of the invention antimicrobial agents in pre-determined amounts, to yield pre-determined concentrations after being dissolved, are pre-deposited in wells where culture media with bacteria are added before the AST. The pre-deposited antimicrobial agents are preferably freeze-dried formulations.

The step of growing, or culturing, the sample/microorganisms therefrom in the AST assay may take place by any known or convenient means. Solid or liquid phase cultures may be used.

Thus for example, in one preferred embodiment, the microorganisms may be cultured on or in a plate or other solid medium, or in a vessel (e.g. a well of a plate) containing a liquid medium, containing the antimicrobial agent and microbial growth may be determined by visualising (e.g. imaging) the microorganisms (i.e. imaging the plate etc.) Thus, the culture is visualised or imaged directly as a means of monitoring or assessing growth. Accordingly in one preferred embodiment the cultures are analysed directly to monitor/assess growth. For example, the cultures may be grown in the wells of a plate and the wells may be imaged.

Alternatively, samples (or aliquots) may be removed (or taken) from the AST test cultures, at intervals, or at different time points and the removed samples (aliquots) may be analysed for microbial growth. This may be done by any means, including for example by means of molecular tests, e.g. nucleic acid based tests, Thus detection probes and/or primers may be used which bind to the microbial cells or to components released or separated from microbial cells. This may include for example nucleic acid probes or primers which may hybridise to microbial DNA. In other embodiments, microbial cells may be detected directly, e.g. by staining, as described in more detail below.

Each antimicrobial agent is used at at least two concentrations, in addition to a positive control in which the microorganism is allowed to grow in the absence of any antimicrobial agent as well as at least one negative control that are cultured in absence of added test aliquot. For example, 2, 3, 4, 5, 6, 7, or 8 or more concentrations of an antimicrobial agent are used. The concentrations used in a dilution series may differ two-fold between respective concentrations.

The term antimicrobial agent includes any agent that kills microorganisms or inhibits their growth. Antimicrobial agents of the present invention may particularly include antibiotics and antifungals. Antimicrobial agents may be microbicidal or microbiostatic. Various different classes of antibiotic are known, including antibiotics active against fungi, or particularly groups of fungi and any or all of these may be used. Antibiotics may include beta lactam antibiotics, cephalosporins, polymyxins, rifamycins, lipiarmycins, quinolones, sulphonamides, macrolides, lincosamides, tetracyclines, aminoglycosides, cyclic lipopeptides, glycylcyclines, oxazolidinones, lipiarmycins or carbapenems. Preferred antifungals of the present invention may include polyenes, imidazoles, triazoles and thiazoles, allylamines or echinocandins. Antimicrobial agents are continuously being developed and it is understood that also future antimicrobials will be possible to analyse with the current invention.

Accordingly, antimicrobial susceptibility may be determined by culturing the microorganisms separated or enriched from the test aliquot, and analysing the AST cultures over a range of time points. As for the clinical sample culture, culture for AST may take place at any temperature that promotes microbial growth, e.g. between about 20° C. and 40° C., or 20 to 37° C., preferably between about 25° C. and 37° C., more preferably between about 30° C. and 37° C. or 30 to 35° C. In one embodiment the AST cultures may be cultured at about 35° C. The AST cultures may be analysed at multiple time points to monitor microbial growth. For example, cultures may be analysed at time points 0, 1, 2, 3, 4, 5, 6, 7, 8, 9, 10, 11, 12, 13, 14, 15, 16, 17, 18, 19, 20, 21, 22, 23 or 24 hours after the initiation of culture. A culture may be analysed immediately after the initiation of culture, where t=0. Cultures may also be analysed at time periods beyond 24 hours after the initiation of culture. Typically cultures might be analysed at 0, 1, 2, 3, 4, 6 and 24 hours after the initiation of culture. However, results obtained and reported in the Examples below show that short incubation times can be sufficient for detecting differential microbial growth e.g. 4 hours. Accordingly, shorter total incubation time of up to 8, 7, 6, 5, 4, 3 or 2 hours may also be used, e.g. analysing every hour or every 2 hours or 90 minutes. As noted above, cultures are generally analysed at two or more time points, e.g. at two or more time points up to 4, 5 or 6 hours of culture.

Many methods for monitoring or assessing microbial growth are known and are used in AST assays, for example including turbimetric measurement, colorimetric determination, light detection, light scattering, pH measurement, spectroscopic measurements, fluorometric detection measuring of degradation products of antibiotics or microbial, measuring nucleic acid content or measuring production of gas, e.g. $CO_2$. Any of these may be used. However, according to a preferred embodiment of the present invention growth may be detected and assessed by determining or assessing the number and/or amount and/or size and/or area of microbial cells in the sample by imaging methods, As noted above, the microbial cells can include cells in colonies and/or aggregates. This may be achieved by assessing or determining the number or amount of microorganisms present in the sample before and/or after growth in presence of antimicrobial agents by any of the methods known to measure or detect microorganisms. Such a determination may involve determining the number and/or size of microbial cells, aggregates and/or colonies. Again, techniques for this are known and available. Thus, growth may be measured by monitoring the number and/or amount and/or size of microorganisms and/or microbial cells and/or colonies and/or aggregates in a sample over time. This may be measured directly or indirectly. The number or amount of microorganisms in a sample may be measured directly by haemocytometry, flow cytometry, or automated microscopy. Microorganisms may be fixed and/or permeabilised prior to detection. Alternatively, microorganisms may be detected under in vivo conditions. Methods for AST assaying by bacterial cell count monitoring using flow cytometry are described in Broeren et al., 2013, Clin. Microbiol. Infect. 19. 286-291. Methods for performing AST assays in which bacteria are grown and enumerated by automated microscopy in multi-channel fluidic cassettes are described by Price et al. 2014, J. Microbiol. Met. 98, 50-58 and by Metzger et al., 2014. J. Microbiol. Met. 79, 160-165, and by Accelerate Diagnostics (see for example WO 2014/040088 A1, US 2014/0278136 A1 and U.S. Pat. No. 8,460,887 B2). In these methods, bacteria are immobilised and grown on a surface, and individual bacteria and/or colonies are assessed for viability and/or growth (including measuring colony growth) by imaging the surface at two or more time points. Such methods may be used according to the present invention. Other methods known are as described by Fredborg et al, J Clin Microbiol. 2013 July; 51(7):2047-53, and by Unisensor (U.S. Pat. No. 8,780, 181) where bacteria are imaged in solution using bright-field microscopy by taking a series of stacked images (object planes) of the solution, and counting the bacteria present in the sample.

Whilst any of the methods based on using imaging to monitor microbial growth may be used, the methods of the invention preferably do not rely on counting individual cells or on monitoring the growth of individual cells or colonies (e.g. on monitoring an increase in size of an individual cell or colony e.g. according to the methods of Accelerate Diagnostics Inc.) Thus, the present invention is not limited to (and in preferred embodiments does not involve) using a fixed position for imaging an AST culture or AST culture sample. Rather, it is preferred according to the present invention to monitor the bulk growth of cells in the AST culture, e.g. by imaging bulk cells in the field of view. The amount (e.g. area) of microbial cell matter (biomass) in the field of view may be determined by imaging. The cells/microbial biomass may be detected directly (e.g. by the microscope or camera etc.) e.g. using bright field microscopy or the microbial cells may be stained for detection, e.g. by adding stain to the AST culture or culture sample after the predetermined or required time period of growth.

In a further particular embodiment, the AST cultures or culture samples may be imaged or visualised directly without immobilising the microbial cells, e.g. without applying a force, such as electrophoresis, to localise the cells to a detection location or surface for imaging.

In such imaging methods, algorithms may be applied to determine a value for the amount of microbial growth from the images according to methods and principles well known in the art. Thus, statistical methods may be applied to the images of microbial cells, based on the number, size, and/or area of microbial cell matter/biomass in the images (e.g. the amount of all the microbial cell matter in the image/field of view, for example total cell matter imaged). Algorithms may be written to take account of different growth patterns and/or morphologies, based on the identity of the microorganism and the antimicrobial agent present in the culture.

Such counting or imaging methods allow a digital phenotypic analysis of the microorganism in the AST assay. Data has been obtained which shows that such digital phenotypic determinations deliver a MIC value similar to that of reference techniques (e.g. microbroth dilution).

A particular advantage of using such methods is that antimicrobial susceptibility testing may be performed on test microbial cultures comprising a wide range of concentrations or amounts of microorganisms, and it is not necessary to use a standardised microbial titer prior to perform the antimicrobial susceptibility testing. A useful feature of the present invention is the ability to use different concentrations of microorganisms. A sample (i.e. a test microbial culture, or microbial culture preparation) comprising at least $10^3$ CFU/ml may be used in the methods of the invention, for example samples (AST test samples) comprising at least $10^4$, $10^5$, $10^6$, $10^7$ $10^8$ or $10^9$ CFU/ml may be used. Alternatively a sample (AST test sample) comprising less than $10^3$ CFU/ml may be used, for example at least $10^2$ CFU/ml. A sample (AST test sample) comprising less than $10^2$ CFU/ml may also be used in the methods of the present invention Although bright field imaging represents one format for assaying the concentration of microbial cells in a sample, in one embodiment of the present invention, microorganisms may be detected by adding a marker that stains microorganisms (i.e. a stain or dye) prior to determining the number or amount of microorganisms the AST test cultures or by methods which utilize an intrinsic property of the microorganism such as e.g. phase contrast or any other method known in the art for quantifying the number of bacteria in the sample. Suitable stains might include coloured or fluorescent dyes, for example Gram staining or other staining for peptidoglycan or DNA staining, as a means of visualising the microorganism. In one particular embodiment of the present invention, DNA within a microorganism may be stained using Vybrant® DyeCycle™. Other DNA stains are well known and available. Indeed the number of stains available in the art for staining bacteria is vast and large numbers of such stains have been documented, including in standard reference texts, and are commercially available, e.g. from Life Technologies. Direct labelling of microorganisms by staining is easy to perform, convenient and cost-effective, and therefore represents a preferred embodiment.

Thus for example, the microorganisms may be grown for the AST assay in wells of a microtiter plate, and the end of the growth periods the dye or stain may be added and the plate wells may be imaged and the number or amount of microorganisms or microbial cell matter may be assessed, by determining the number and/or size of microbial cells, aggregates or colonies e.g. by counting or imaging. Alternatively, microorganisms may be enumerated using a flow cytometer or similar type of instrument, for example the Aquila 400 instrument from Q-linea AB (Sweden), e.g. as described in U.S. patent application No. 61/979,319.

In an alternative embodiment a microorganism may be specifically labelled via a biological feature within or on the microorganism. A "biological feature" may for example be a molecule in or on the microorganism e.g. a protein or other biomolecule expressed or located on the cell surface. For example a label, e.g. a coloured or fluorescent label, may be coupled to a protein or other affinity binding molecule that binds specifically to a particular biological feature. In one embodiment the protein may be a lectin, affibody or antibody, or antibody fragment. The microorganisms labelled in this way may be detected e.g. enumerated as previously described.

In a further embodiment proximity probes may be used to detect a specific biological feature within or on a microorganism.

In a further alternative embodiment of the present invention the microorganisms may be detected and enumerated using a padlock probe and RCA-based amplified single molecule detection (ASMD) method. Such methods enable single microbial cells to be detected and counted. Thus, the microorganism may be detected by binding of the padlock probe and the number of microorganisms in a sample may be measured indirectly by an amplified signal generated via RCA of the circularised padlock probe. Each RCA product (blob) may be indicative of a single microorganism. Microorganisms may be lysed and padlock probes may be used which are designed to hybridise to one or more nucleotide sequences of the microorganisms. This may include a step of separating DNA, and preferably of selectively separating, or enriching for, microbial DNA. Since in the AST assay the cultures are usually less complex than in the step of initial clinical sample culture, a simplified protocol for separating or enriching microbial DNA may be used, involving for example filtration to separate microorganisms and microbial cell lysis or simply direct microbial cell lysis.

Alternatively, affinity binding molecules may be used which bind to one or more molecules present on a microorganism or within a lysed microorganism, such an affinity probe being provided with an nucleic acid label or tag to which a padlock probe may hybridise i.e. akin to an immunoRCA detection procedure. Similarly proximity probes may be used to bind to a target in or on a microorganism and the nucleic acid domains of the proximity probes may be used to template the ligation of a padlock probe and optionally also prime its amplification by RCA. Procedures for this are widely known and described in the literature. Circle-to-circle amplification (C2CA) as described for example in Dahl et al, 2004, PNAS USA, 101, 4548-4553 and WO 03/012119 may be used for signal amplification. The number of microorganisms in a sample can therefore be estimated by counting the number of blobs, which may be labelled e.g. fluorescently-labelled as described above 'blobs' within a sample. This thus provides another convenient means of obtaining a digital phenotypic susceptibility readout.

It is generally speaking advantageous in performing an AST assay for the microbial culture under test to be pure, i.e. for there to be a single microorganism. Thus, in a preferred embodiment, method of the invention is performed if a single microorganism is identified in a preceding microbial identification test (e.g. a molecular ID test performed on an aliquot removed from the clinical sample culture). However, this is not an essential feature, and it is possible to use microbial detection methods based on visualisation or imaging to perform AST assays, for example methods as provided by Accelerate Diagnostics which use imaging of bacteria on a surface and not in solution, or indeed methods in which labelled microorganisms are detected in fluidic systems e.g. the automated microscopy fluidic cassette-based systems of Price et al. 2014, J. Microbiol. Met. 98, 50-58 and by Metzger et al., 2014. J. Microbiol. Met. 79, 160-165, discussed above. Any cell-by-cell detection, or shape recognition and/or identification methods may be used for AST assaying of samples which contain more than one microorganism. It is further known that different microorganisms may be affected differently by the same antibiotic and therefore the appearance of an organism upon treatment with a specific antibiotic may be used for identification and AST determination for each microorganism in co-cultures Conveniently the methods of the invention may be automated. Any one of more of the steps may be automated, preferably any or all of steps (a) to (f). Various specific or preferred steps discussed above lend themselves well to automation, for example the AST assaying and the microbial/colony counting methods. Automatic culturing methods have already been developed, including for blood culture methods for microbial identification and/or AST assaying and can be used or adapted for use according to the present invention. Automation would provide the advantage of speed and ease of operation, as well as multiplexing ability, which are of importance in clinical laboratory setting and especially important in the diagnosis of sepsis.

According to a further aspect of the invention, there is provided a device for determining the antimicrobial susceptibility of a microorganism in a clinical sample, the device comprising: a test aliquot removal unit for removing a test aliquot from a clinical sample culture in a culture vessel; a transfer unit for transferring microbial cells isolated from the test aliquot into a culture medium suitable for microbial cell growth to thereby prepare a microbial culture preparation; an inoculation unit for inoculating a series of test microbial cultures for an antibiotic susceptibility test (AST); a measurement unit for determining concentration of microbial cells and for assessing (e.g. monitoring) the degree of microbial growth in the series of test microbial cultures; and a controller, wherein the controller is configured to: control the test aliquot removal unit to remove the test aliquot from the culture vessel when the culture in the culture vessel is less than 0.5 McFarland units; control the measurement unit to measure the concentration of microbial cells in the microbial culture preparation and/or the concentration of microbial cells in the test microbial cultures; control the device to adjust the concentration of microbial cells in said microbial culture preparation and/or said test microbial cultures to a predetermined or desired value; and determine at least one MIC value for at least one antimicrobial agent, thereby to determine the antimicrobial susceptibility of said microorganism in said clinical sample.

Preferably, the device is arranged to perform the method of any preceding aspect, optionally including any of the preferred/optional features of the foregoing methods.

As noted above, the controller is configured to control the test aliquot removal unit to remove the test aliquot from the culture vessel when the culture in the culture vessel is less than 0.5 McFarland units. Thus, in certain embodiments the controller may be configured to control the test aliquot removal unit to remove the test aliquot from the culture vessel when the culture in the culture vessel is less than 0.30, 0.25, 0.20, 0.10, 0.05, 0.01, 0.005, 0.001, 0.0005, or 0.0001 McFarland units, or the equivalent thereof, as discussed above. Thus, in certain embodiments, the controller may be configured to control the test aliquot removal unit to remove the test aliquot from the culture vessel when the culture in the culture vessel is less than $10^8$ CFU/ml, less than $5 \times 10^7$ CFU/ml, less than $10^7$ CFU/ml, less than $5 \times 10^6$ CFU/ml, less than $10^6$ CFU/ml, more particularly less than $5 \times 10^5$ CFU/ml, less than $10^5$ CFU/ml, and most particularly less than $5 \times 10^4$ CFU/ml or less than $10^4$ CFU/ml, less than or equal to $5 \times 10^3$ CFU/ml or less than or equal to $10^3$ CFU/ml, or less than $10^3$ CFU/ml, e.g. less than or equal to $5 \times 10^2$ CFU/ml or less than or equal to $10^2$ CFU/ml.

As noted above, the controller is configured to control the device to adjust the concentration of microbial cells in said microbial culture preparation and/or said test microbial cultures. The meaning of "adjusting" the concentration is discussed in detail in relation to the method described herein (the same definition applies here), and is briefly summarised below.

By "adjusting the concentration of microbial cells in said microbial culture preparation or said test microbial cultures", it is meant that the concentration of microbial cells is physically or virtually changed. Thus for example the concentration (or number) of microbial cells in the microbial culture preparation may be physically increased (e.g. by culturing the microbial culture preparation for a period of time to allow the microbial cells to grow) or physically decreased (e.g. by dilution, e.g. by liquid medium) prior to inoculating the test microbial cultures, or in the course of inoculating the test microbial cultures (e.g. by selecting an appropriate amount (e.g. volume) to be used to set up the test cultures, either by adding to solid (e.g. freeze-dried) antibiotics or by dilution when a portion or aliquot of the microbial culture preparation is added to a volume of antibiotic and/or culture medium for the AST test. Therefore, the device may comprise a concentration adjustment unit which is controlled by the controller to physically change the concentration of microbial cells in said microbial culture preparation or said test microbial cultures. The concentration adjustment unit may comprise a culturing unit for culturing the microbial culture preparation and/or may comprise a reservoir comprising a diluent to be added to the microbial culture preparation and/or to the test microbial cultures.

As discussed above in relation to the method, the controller may be configured to control the concentration adjustment unit to adjust the microbial culture preparation and/or the test microbial cultures to comprise any defined or pre-determined concentration of microbial cells, provided the concentration of microbial cells in the test microbial cultures that are used to obtain an AST value is known.

In one embodiment the controller is configured to control the device (or the concentration adjustment unit) to adjust the concentration of microbial cells in the microbial culture preparation to a standard concentration, for example 0.5 McFarland units. In another embodiment, the controller is configured to control the device (or the concentration adjustment unit) to adjust the concentration of microbial cells in the microbial culture preparation to a concentration that is less than a standard concentration.

The controller may be configured to control the concentration determination unit to measure the concentration of microbial cells again after or during controlling the device (or the concentration adjustment unit) to adjust (physically) the concentration of microbial cells in the microbial culture preparation or said test microbial cultures.

The MIC value for at least one antimicrobial agent determined by the controller may be a standard MIC value.

Alternatively, instead of physically adjusting the concentration of the microbial cells, a virtual adjustment (an algorithmic correction) may be made, based on the measured concentration of the microbial cells. That is, a virtual adjustment may take place, using e.g. mathematical methods to account for (e.g. to normalise) the concentration of cells present in the microbial culture preparation or in the test microbial cultures. This may be done using algorithms according to methods known in the art. The parameters used to adjust the concentration of microbial cells may be obtained empirically, and may vary depending on the identity of the microorganism and the antimicrobial agent that is being used. For instance, the adjustment may be significant e.g. if a microorganism is known to secrete enzymes which degrade an antimicrobial agent, or if the microorganism forms a biofilm.

In embodiments in which a virtual adjustment is made, the controller may be configured to adjust the at least one MIC value based on the determined concentration of microbial cells in said microbial culture preparation or said test microbial cultures to obtain at least one standard MIC value.

Preferably, the test aliquot removal unit may be configured to receive a needle and a syringe. The needle, and optionally also the syringe, may be a single-use consumable.

The device may be configured to receive an isolation unit (which may be a single-use consumable) for isolating microbial cells from said test aliquot. The isolation unit may comprise a lysis reservoir for receiving a portion of the test aliquot, and a reservoir for containing a lysis buffer, connected to the lysis reservoir. The isolation unit may comprise a filter connected for filtering the sample after lysis, the filter being configured to retain bacteria on the filter, preferably wherein said filter comprises a pore size in the range of 0.1 to 0.65 µm. The isolation unit may comprise a wash reservoir for containing a wash buffer or culture medium for back-flushing the filter to re-suspend the microbial cells. The device may comprise an isolation unit as described above.

Preferably, the transfer unit and inoculation unit comprise pipetting assemblies. Instead of comprising a pipetting assembly, the transfer unit may be configured to receive a fluidic interface unit (which may be a single-use consumable) for transferring microbial cells isolated from the test aliquot into the culture medium suitable for microbial cell growth to thereby prepare the microbial culture preparation. Preferably, the culture medium will be a liquid culture medium. The inoculation unit may be configured to receive a panel comprising wells within which are pre-deposited antimicrobial agents in pre-determined amounts. The pre-deposited antimicrobial agents are preferably freeze-dried formulations. The panel is preferably a single-use consumable. The device may comprise a panel as described above.

The measurement unit may comprise a concentration determination unit for determining concentration of microbial cells and a separate assessment unit for assessing the degree of microbial growth in the series of test microbial cultures.

The concentration determination unit may determine the concentration by any method known in the art. For example, the concentration determination unit may be operable to determine the concentration by counting (by haemocytometry or flow cytometry for example), by turbidimetry or by imaging.

The assessment unit may be configured to assess (e.g. monitor) the degree of microbial growth by at least one of the following methods: imaging, turbidimetric measurement, colorimetric determination, light detection, light scattering, pH measurement, spectroscopic measurements, fluorometric detection measuring of degradation products of antibiotics or microbial, measuring nucleic acid content or measuring production of gas, e.g. $CO_2$. Preferably however, the assessment unit is an imaging unit, and may comprise for example a camera and/or a fluorescence microscope and/or a bright field microscope.

Alternatively, the measurement unit may perform the dual functions of determining concentration of microbial cells and assessing the degree of microbial growth in the series of test microbial cultures (i.e. there is not a separate concentration determination unit and assessment unit, only a single measurement unit which performs both functions). In such a case, the measurement unit is preferably an imaging unit, and may comprise for example a camera and/or a fluorescence microscope and/or a bright field microscope.

The device may comprise a culture unit configured to receive the culture vessel and to culture it, preferably wherein the culture vessel is a blood culture flask. The device may comprise a culture vessel, which is preferably a blood culture flask.

The device may be configured to receive a filter for filtering the test aliquot, The filter may comprise a pore size of at least 100 µm, i.e. sized so as to filter out any resin particles present in the blood culture flask. The filter may comprise a pore size of less than 1000 µm, and preferably may comprise a pore size of less than 500 µm. The device may comprise such a filter.

The invention will now be described in the detailed description and in the Examples below, with reference to the following drawings in which:

FIG. 1 is a schematic diagram illustrating a device for determining the antimicrobial susceptibility of a microorganism in a clinical sample, according to an embodiment of the present invention.

Figure 2:
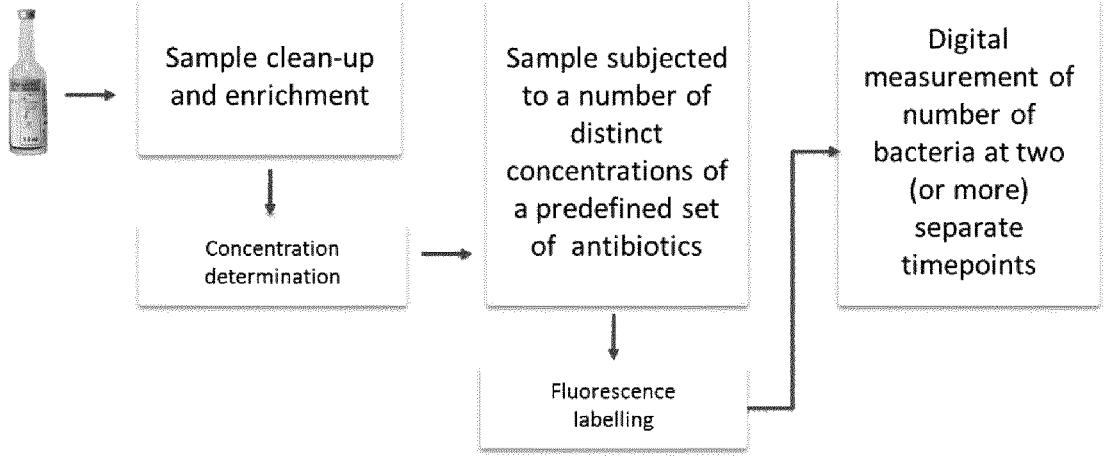
Figure 2:
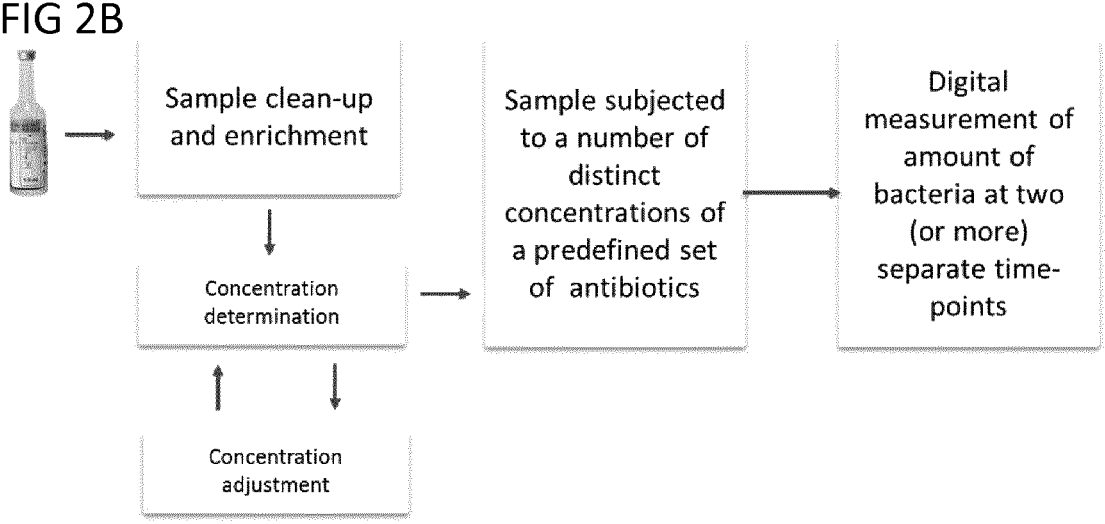
Figure 2:
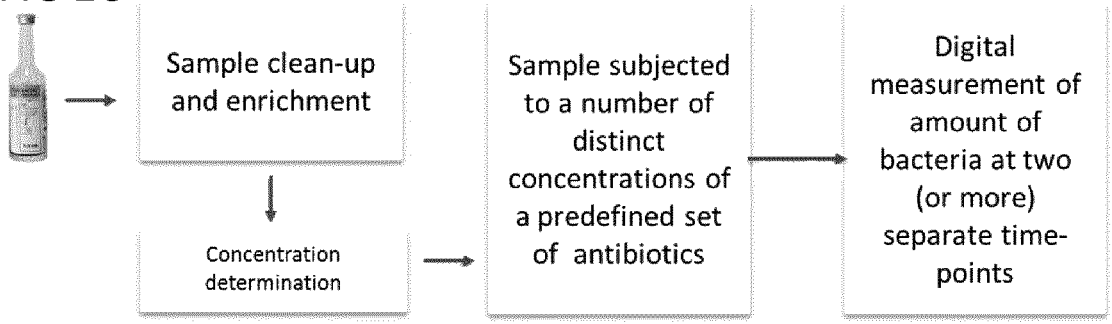

FIG. 2 shows a series of workflows indicating possible alternative embodiments of the present invention. FIG. 2A: Microbial cells are fluorescently labelled and are detected by fluorescence microscopy, Fluorescence-based AST requires a labelling step before microbial growth may be monitored (assessed). FIG. 2B: Workflow with a concentration adjustment step included after the concentration of microbial cells in the culture medium preparation. The adjustment step could be continued culturing or dilution of the sample to reach a pre-defined concentration before starting the AST. FIG. 2C: Non-fluorescent read-out—microbial growth is assessed by imaging, or other technique which does not require fluorescent labelling.

FIG. 3 shows examples of bright-field microphotographs of bacteria showing different morphology of bacteria after exposure to antibiotics for four hours. Images A-C show $E.\ coli$: A) no antibiotic, B) Ciprofloxacin and C) Meropenem. Image D shows $S.\ aureus$, which is known to form cellular aggregates in the presence of blood.

Figure 4:
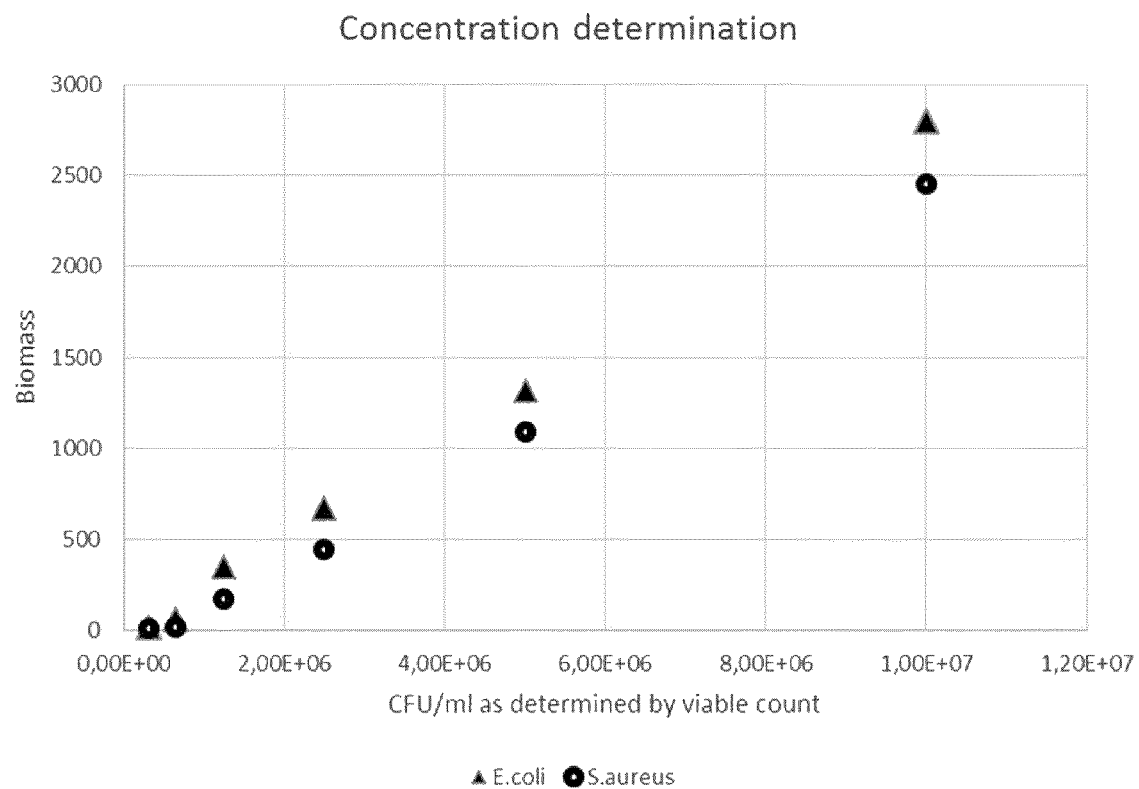

FIG. 4 shows a comparison of measuring the concentration of microbial cells in a sample by imaging with conventional techniques. The concentration of microbial cells determined by imaging was found to correlate well with conventional techniques.

Figure 5A:
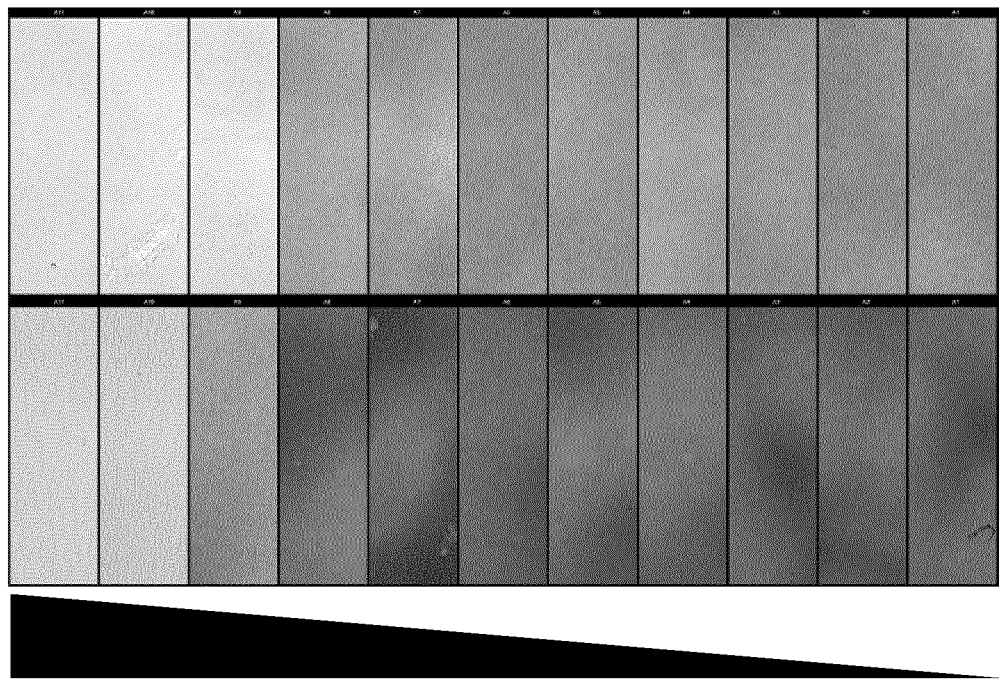
Figure 5B:
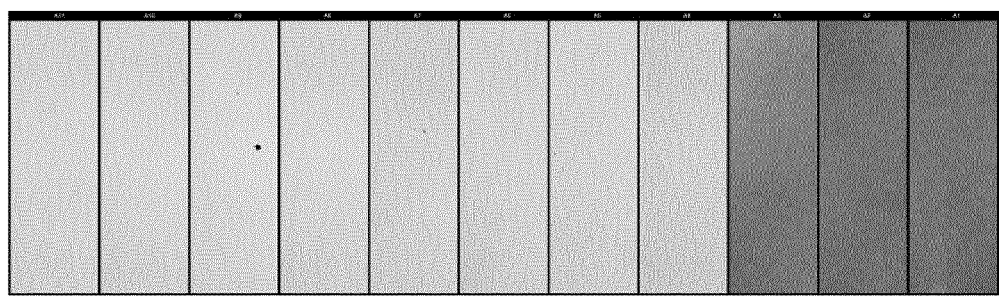
Figure 5:
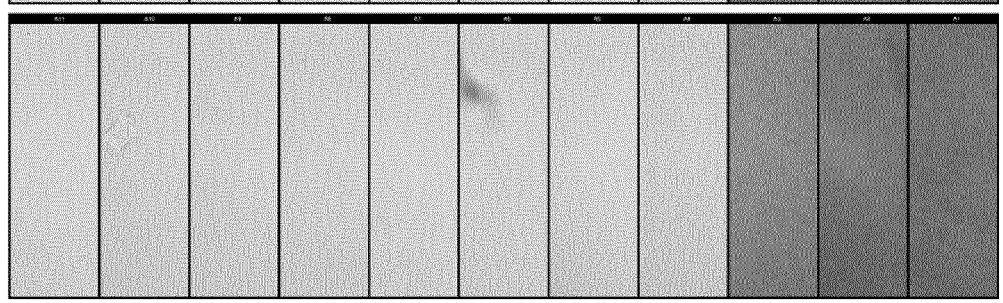

FIG. 5 shows the effects of the concentration of microbial cells used to initiate the AST assay affect the MIC values obtained. FIG. 5A shows that different titers of gentamicin resistant $E.\ coli$ may provide different MIC results. FIG. 5B shows the reproducibility of the present method where the same titer is used to initiate the AST assay: AST assays performed on separate days using the same microbial titer provided the same MIC results.

Figure 6:
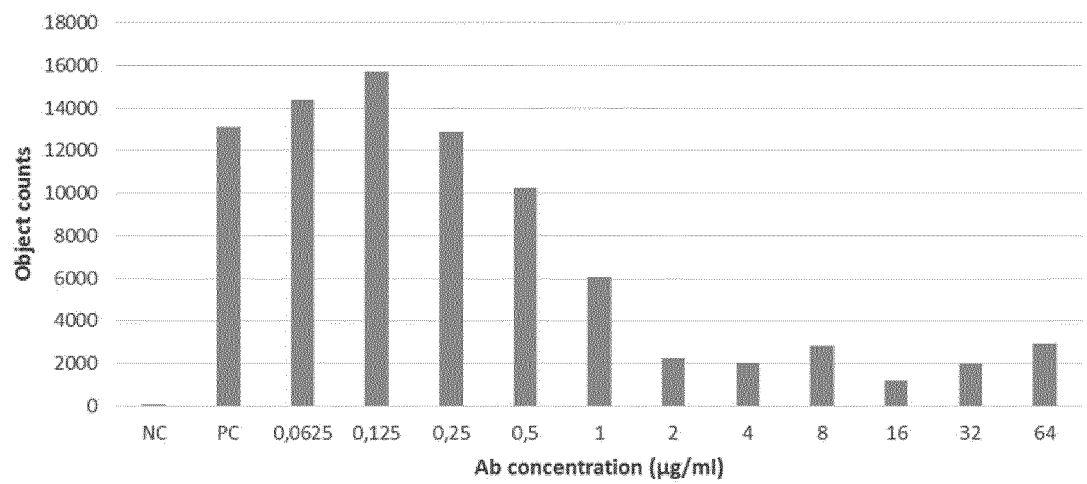
Figure 6:
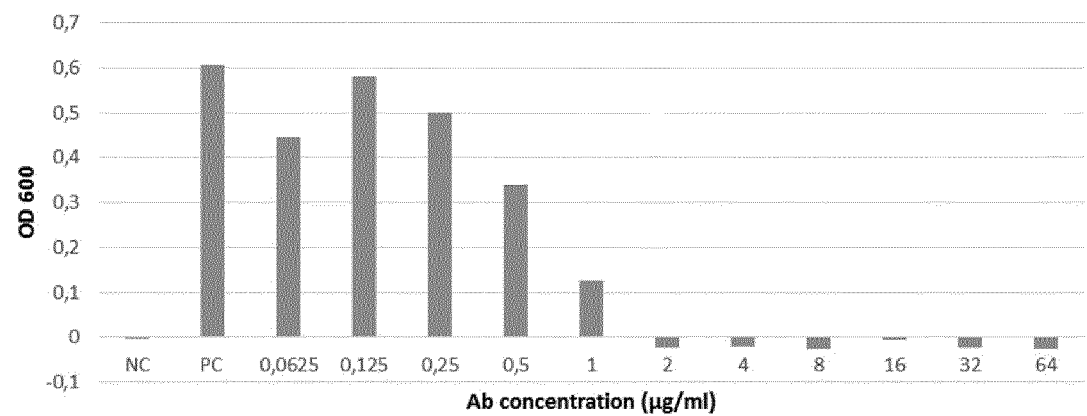

FIG. 6 shows that MIC values obtained by measuring growth by imaging correlate well with the MIC values obtained by turbidity measurement (OD600). FIG. 6A: MIC determination by monitoring growth by imaging after incubation for 4 hours. FIG. 6B: MIC determination by monitoring growth by turbidity measurement after incubation for 24 hours.

FIG. 7 shows that MIC values can reproducibly be measured by imaging; three separate AST assays were performed on separate days using separate samples adjusted to the same microbial titer level. FIG. 7A: MIC determination by monitoring growth by imaging after incubation for 4 hours. Data from each repeat was found to correlate well. FIG. 7B: Confirmation of MIC values by measuring turbidity after incubation for 24 hours.

DETAILED DESCRIPTION

FIG. 1 is a schematic diagram illustrating a device for determining the antimicrobial susceptibility of a microorganism in a clinical sample, according to an embodiment of the present invention.

The device 10 shown in FIG. 1 comprises: a test aliquot removal unit 12; an isolation unit 14; a transfer unit 16; a reservoir 17; an inoculation unit 18; a microtiter plate 20 comprising a series of test microbial cultures; a concentration determination unit 22; a concentration adjustment unit 24; an assessment unit 26; and a controller 28. In use, a culture vessel 1 (e.g. a blood culture flask) is placed inside the device 10.

The test aliquot removal unit 12 comprises a needle 12a and syringe 12b, which together are provided as a consumable for a single use. The test aliquot removal unit 12 is operable to remove a test aliquot from the culture vessel 1.

The isolation unit 14 comprises: a first filter 14a for removing resin beads present in the blood culture vessel from the test aliquot, the first filter having a pore size of approximately 100 µm; a buffer reservoir 14b comprising a lysis buffer; a lysis reservoir 14c in which a portion of the test aliquot and lysis buffer are mixed and lysis takes place; a second filter 14d connected to the a lysis reservoir 14c for capturing microbial cells, the second filter 14d having a pore size of approximately 0.2 µm; and a wash reservoir 14e for holding a wash buffer or culture medium for back-flushing the microbial cells off of the filter. The isolation unit 14 is provided as a single-use consumable.

The transfer unit 16 comprises a fluidics or pipetting assembly for transferring the microbial cells back-flushed from the filter into a reservoir 17 to form a microbial culture preparation. Parts of the transfer unit 16 which come into contact with the sample (pipette-tips, syringes etc.) are provided as single-use consumables.

The inoculation unit 18 comprises a pipetting assembly for inoculating the microtiter plate 20 using the microbial culture preparation. The wells of the microtiter plate (not shown) contain at least two different concentrations of at least one antimicrobial agent, a negative control (i.e. comprising only medium) and a positive control sample (i.e. comprising no antimicrobial agent). The microtiter plate 20 is provided as a single-use consumable. The concentration determination unit 22 comprises an imager for determining the concentration using an imaging method.

The concentration adjustment unit 24 comprises a reservoir 24a comprising a diluent for diluting the microbial cells in the microbial culture preparation 17 and/or the concentration of microbial cells in the test microbial cultures. The concentration adjustment unit 24 also comprises a culturing unit 24b.

The assessment unit 26 is an imaging unit comprising a bright field microscope and a camera. A specific area of the specimen is covered in a single xy-aligned image the size of which is dependent on the optical properties of the imaging apparatus. For each position in xy-space, one or more 2D images are collected at different intervals along the optical or z axis. Thus, a series, or stack of 2D images can be generated, providing 3D information of a sample volume. Once extracted, the 3D information inherent in the 2D image stacks is utilized to estimate/infer/deduce the total cell mass present in the analysed volume.

The controller 28 is in communication with each stage of the device which is configured to carry out a controllable function (for example: the test aliquot removal unit 12; the isolation unit 14; the transfer unit 16; the inoculation unit 18; the concentration determination unit 22; the concentration adjustment unit 24; and the assessment unit 26). For clarity, the lines of communication between the controller and other parts of the device are not shown.

The controller 28 is operable to operate in two modes. In the first, the controller 28 controls the device 10 to physically adjust the concentration of microbial cells in said microbial culture preparation 17 or in the test microbial cultures in the microtiter plate 20. Either the concentration (or number) of microbial cells in the microbial culture preparation 17 or in the wells of the microtiter plate 20 is physically increased if necessary (e.g. by culturing for a period of time to allow the microbial cells to grow) or physically decreased (e.g. by dilution using diluent in the concentration adjustment unit 24). The controller 28 may also control the concentration determination unit 22 to measure the concentration of microbial cells again after or during controlling the device 10 (or the concentration adjustment unit 24) to adjust the concentration of microbial cells.

In the second mode, the controller 28 is configured such that the concentration of microbial cells is not physically adjusted, but instead a virtual adjustment (an algorithmic correction) is made, based on the measured concentration of the microbial cells. In either case, the controller 28 is configured to calculate a standard MIC value.

Example 1—Method for Performing AST 5 ml of a cultured clinical sample is removed from a blood culture flask, and filtered using a 100 µm filter to remove resin particles from the culture medium. The sample is mixed with a 10 ml of lysis buffer capable of selectively lysing any non-microbial cells present in the sample, and incubated for a sufficient amount of time for the non-microbial cells to be lysed. The resulting lysate is filtered through a 0.22 µm filter. Liquid components of the lysate (including components of the lysed non-microbial cells) pass through the filter, whereas microbial cells present in the sample are retained on the filter.

The retained microbial cells are resuspended in a suitable microbial culture medium to form a microbial culture preparation, by back-flushing the filter with culture medium (i.e. flowing the culture medium in the opposite direction to filtration). The concentration of microbial cells present in the microbial culture preparation is measured at this stage, and if necessary, diluted with additional culture medium in order to reduce the concentration, or allowed to grow further at this stage in order to increase the concentration.

Once a suitable concentration of microbial cells has been obtained, 100 µl aliquots of the microbial culture preparation are dispensed into wells of a microtiter plate. The wells of the microtiter plate contain at least two different concentrations of at least one antimicrobial agent. A negative control (i.e. comprising only medium) is also set up at this stage and a positive control sample (i.e. comprising no antimicrobial agent).

The microtiter plate is placed in an oCelloScope reader in an InnuCell111 incubator. A bottom search for focus is performed on each inoculated well and each well is read at intervals of 1 hour. A total of 6 repeats are performed (a total of 7 images are taken at time points from 0 to 6 hours after the initiation of the AST assay. The degree of microbial growth in each growth condition is monitored by imaging, by measuring the amount of microbial biomass in each well.

Example 2—Morphology of Bacteria in an AST Assay is Affected by the Growth Conditions Present Bacterial cells were spiked into blood culture flasks (BCF). Samples A-C were spiked with *E. coli* with blood at a concentration lower than 0.5 McFarland and subjected to sample clean-up and recovered in MH-media. Aliquots of the recovered bacteria were dispensed into a micro-titerplate with freeze dried antibiotics at varying concentrations and allowed to grow for four hours before imaging. Sample A did not contain an antibiotic. Sample B was added to Ciprofloxacin. Sample C was added to Meropenem. An image of the microbial cells after four hours' growth is shown in FIG. 3 A-C at a single concentration of each antibiotic, indicating that the morphology of microbial growth may be affected by the presence and nature of the antibiotic added to sample.

Sample D was spiked with *S. aureus*, which is known to form aggregates in the presence of blood. The sample was cultured for a sufficient period of time to ensure that the aggregation of bacteria before sample clean-up. The same procedure was then performed as described for sample A-C.

Example 3—Concentration Determination Using Imaging and Measuring Biomass in Microphotograph of Sample A sample of bacteria, (*E. coli* or *S. aureus*) was diluted in MH-media and aliquots of the dilution were dispensed into an optical microtiter plate. Viability of the bacteria in the original solution was determined by plating and counting CFU after overnight growth on TSA (Tryptic Soy Agar) plates. Images of the microtiter plate were acquired at T 0 h of the wells and the biomass of bacteria were recorded and to compared to expected viable count (see FIG. 4). Using the current method it is possible to measure the concentration of bacterial solutions well below 0.5 McFarland.

Example 4—The MIC Value Obtained in an AST Assay May Vary Depending on the Initial Concentration of Microbial Cells

*E. coli* grown in blood+BCF media were recovered via a clean-up procedure to remove blood components and only retain viable bacteria in MH-media. Adjustment of the recovered bacteria were made to ensure different titers are used at start of the AST. AST assays were set up to a starting concentration of $3 \times 10^5$ CFU/ml (Lane A) and $2 \times 10^6$ CFU/ml (Lane B) of a gentamicin resistant *E. coli* strain. Aliquots of the recovered bacteria were dispensed into a microtiter plate with freeze dried antibiotics at varying concentrations and allowed to grow for four hours before imaging. Images of the wells of the microtiter plate for each concentration of gentamicin are shown in FIG. 5A. Shown are microphotographs from a series of different concentration of antibiotics in two-fold dilutions ranging from 64 mg/l to 0.0625 mg/l of gentamicin. The higher bacterial titer (Lane B) show growth in presence of higher concentration of antibiotics, and thus has a higher MIC value. This demonstrates the requirement for concentration determination before AST. In contrast to this, the present method demonstrates good reproducibility when the same concentration of microbial cells is used to set up separate repeats of an AST assay. Lane A and Lane B were set up with bacterial cultures adjusted to have the same titer at the start of the AST on different days. Aliquots of a gentamicin sensitive strain of *E. coli* were dispensed into a microtiter plate as above, and allowed to grow for four hours before imaging. Images of the wells of the microtiter plate for each concentration of gentamicin are shown in FIG. 5B. The experiments performed on different days showed good reproducibility, highlighting the need to determine the concentration of microbial cells in the culture preparation to interpret the data obtained from the AST assay.

Example 5—Determination of AST by Imaging

Sample preparation as in Example 1 was performed on BCF-cultures spiked with *E. coli* and an aliquot was withdrawn with before the culture reached 0.5 McFarland units, i.e. before they were indicated positive in the blood culture cabinet. After recovery of bacteria from the filter, aliquots of the sample were directly added to an optical microtiter plate with freeze dried antibiotics (Sifin diagnostics GmbH.) containing selected antibiotics. The microtiter plate was imaged in an oCelloScope reader at time 0 (h) and 4 hours. The same microtiter plate was allowed to continue to grow for 24 hours and read with a turbimetric assay to control for the rapid AST generated by imaging.

The data obtained using the rapid AST generated by imaging after 4 hours correlated well with the data obtained using a turbimetric assay after 24 hours (FIG. 6). Both the rapid AST and the 24 hour AST provided a MIC estimation of 1 µg/ml, both starting from a culture which had not reached 0.5 McFarland units. The same strain was independently shown to yield an AST of 1 µg/ml when tested using an EUCAST validated method at a certified lab, starting from a 0.5 McFarland culture.

An aliquot of the sample was plated onto a TSA (Tryptic Soy Agar) plate to make an independent measurement of the concentration of bacteria present in the sample used to perform the AST in this experiment and this was found to be $2 \times 10^6$ CFU/ml.

Example 6—Further Determination of AST by Imaging

*E. coli* were spiked into blood culture flasks (BCF) with blood at a concentration lower than 0.5 McFarland units. A sample was taken and subjected to sample clean-up and recovered in MH-media. Aliquots of the recovered bacteria were dispensed into a microtiter plate with freeze dried antibiotics at varying concentrations and allowed to grow for four hours before imaging. Algorithms for quantifying the biomass of bacteria were used to obtain quantitative data from the images. FIG. 7A shows triplicate measurements done on three different days of both the read-out after four hours using images and image algorithm analysis. Optical density measurement after 24 hours growth measured using OD600 are shown in FIG. 7B. AST determined by image analysis was found to correlate well with data obtained from measuring optical density. D02961, D02979 and D02992 denote the different experiments.

Example 7—Determination of AST of Clinical Isolates

Dilutions of two different bacterial clinical isolates were seeded into an aerobic blood culture flask (Bactec, Becton Dickinson) at an estimated concentration of either 1 or 10 CFU/ml blood. Before seeding, the BCF had been filled with human blood from healthy donors. Aliquots from the dilution series were plated on agar and grown over night for viable count. Target concentration was 10 or 100 CFU seeded in 0.5 ml per BCF, corresponding to approximately 1 or 10 CFU/ml blood. The seeded BCF were allowed to incubate for 8 hours at 35° C. and a 5 ml aliquot were taken for subsequent AST. Another aliquot from the same BCF was used for determination of viable count after 8 hours' growth in the BCF.

A 5 ml aliquot of the cultured clinical isolate from the blood culture flask was filtered using a 100 µm filter to remove resin particles from the culture medium. The sample was thereafter mixed with a 10 ml of lysis buffer capable of selectively lysing any non-microbial cells present in the sample, and incubated for a sufficient amount of time for the non-microbial cells to be lysed. The resulting lysate was filtered through a 0.2 µm filter. Liquid components of the lysate (including components of the lysed non-microbial cells) passed through the filter, whereas microbial cells present in the sample were retained on the filter.

The retained microbial cells were re-suspended in liquid Mueller Hinton broth medium to form a microbial culture preparation, by back-flushing the filter with culture medium (i.e. flowing the culture medium in the opposite direction to filtration). 100 µl aliquots of the microbial culture preparation were then dispensed into wells of a microtiter plate.

The wells of the microtiter plate contained between 5 and 13 different concentrations of an antibiotic and different antibiotics. A negative control (i.e. comprising a blood sample with no seeded bacteria) and a positive control sample (i.e. an aliquot of the sample from a seeded BCF but into a well with no antimicrobial agent) were also set up at this stage.

The microtiter plate was placed in an oCelloScope reader in an InnuCell-111 incubator. Focus was performed on each inoculated well and each well was read at intervals of 1 hour. A total of 5 images were taken at time points from 0 to 4 hours after the initiation of the AST assay. The degree of microbial growth in each growth condition was monitored by imaging, by measuring the amount of microbial biomass in each well.

Viable count of the sample before seeded into the BCF and after 8 hour of culture are as shown below in Table 1.

TABLE 1 viable count of microbial cells before and after culture

| Exp. No.# | Isolate | CFU spiked/ BCF | Actual mL blood/ bottle** | Spike CFU/ mL blood | CFU/ml after 8 h culture |
|---|---|---|---|---|---|
| 1 | QM006 | 96 | 17 | 6 | 7.0E+04 |
| 2 | QM006 | 32 | 13 | 2 | 7.3E+04 |
| 3 | QM006 | 103 | 14 | 7 | 1.4E+06 |
| 4 | QM006 | 34 | 10 | 3 | 9.1E+05 |
| 5 | QM006 | 69 | 11 | 6 | 9.8E+05 |
| 6 | QM006 | 23 | 12 | 2 | 3.6E+05 |
| 7 | QM006 | 103 | 10 | 10 | 2.8E+06 |
| 8 | QM006 | 34 | 7 | 5 | 1.3E+06 |
| 9 | QM006 | 95 | 16 | 6 | 1.1E+06 |
| 10 | QM006 | 9 | 13 | 1 | 1.0E+05 |
| 1 | QM171 | 95 | 12 | 8 | 4.7E+05 |
| 2 | QM171 | 32 | 10 | 3 | 3.9E+05 |
| 3 | QM171 | 88 | 11 | 8 | 1.2E+06 |
| 4 | QM171 | 29 | 9 | 3 | 4.7E+05 |
| 5 | QM171 | 91 | 13 | 7 | 6.3E+05 |
| 6 | QM171 | 30 | 14 | 2 | 4.0E+05 |
| 7 | QM171 | 99 | 12 | 8 | 7.1E+03 |

Experiment number only to be used as a guide to Table 1.
**Measured as the total volume recovered from the BCF minus the assumed 27.5 ml BCF media in the BCF and 0.5 ml seeded bacteria.
All samples were taken well below 0.5 McFarland concentration in the cultured sample.

Microphotographs from the different wells were analysed to generate a numerical value of the biomass in the well and this was used as a marker of growth. From the growth a minimal inhibitory concentration was determined and compared to MIC obtained using a reference method, broth micro-dilution. The reference MIC value was conducted by taking one to three colonies of the bacterial strain from an agar plate with pure culture and adjust the concentration to 0.5 McFarland. The adjusted solution was then further processed in line with ISO 20776 guidelines and MIC were determined after 16-20 hours growth by estimating the turbidity in the sample. A sample was determined to Pass (P) if within +/−1 two-fold dilution from the reference MIC.

TABLE 2

MIC calculated from microphotographs.

| Antibiotic | Isolate | Experiment repeat no. | | | | | | | | | Reference | P | F | % Passed | % Passed |
| --- | --- | --- | --- | --- | --- | --- | --- | --- | --- | --- | --- | --- | --- | --- | --- |
| | | 1 | 2 | 3 | 4 | 5 | 6 | 7 | 8 | 9 | | | | | |
| Cefotaxime | QM006 | >8 | >16 | >16 | >16 | >16 | >16 | >16 | >16 | >16 | >8 | 10 | 0 | 100 | 100 |
| | QM171 | 8 | >16 | >16 | >16 | >16 | 16 | 16 | | | >8 | 7 | 0 | 100 | |
| Ceftazidime | QM006 | 8 | 16 | 8 | 8 | 8 | 16 | 8 | 16 | 8 | 16 | 9 | 0 | 100 | 100 |
| | QM171 | 2 | 2 | 2 | 2 | 2 | 2 | 1 | | | 2 | 7 | 0 | 100 | |
| Ciprofloxacin | QM006 | >4 | >4 | >4 | >4 | >4 | >4 | >4 | >4 | >4 | >4 | 10 | 0 | 100 | 100 |
| | QM171 | 0.5 | 0.5 | 0.5 | 0.5 | 0.5 | 0.5 | 0.125 | | | 0.25 | 7 | 0 | 100 | |
| Gentamicin | QM006 | 16 | 16 | 16 | 16 | 16 | 16 | 16 | 16 | 16 | >16 | 9 | 0 | 100 | 100 |
| | QM171 | 0.5 | 0.5 | 0.5 | 0.5 | 0.5 | 0.5 | 0.25 | | | ≤0.5 | 7 | 0 | 100 | |
| Meropenem | QM006 | ≤0.5 | ≤0.5 | ≤0.5 | 1 | ≤0.5 | ≤0.5 | ≤0.5 | ≤0.5 | ≤0.5 | ≤0.5 | 9 | 0 | 100 | 100 |
| | QM171 | ≤0.5 | ≤0.5 | ≤0.5 | ≤0.5 | ≤0.5 | ≤0.5 | ≤0.5 | | | 1 | 7 | 0 | 100 | |

The invention claimed is:

1. A method for determining the antimicrobial susceptibility of a microorganism in a clinical sample said method comprising:
   a) providing a clinical sample culture of a clinical sample in a culture vessel containing culture medium;
   b) removing a test aliquot from said clinical sample culture in said culture vessel, wherein said aliquot is removed when the culture in the culture vessel is less than 0.5 McFarland units;
   c) selectively isolating microbial cells from said test aliquot to separate microbial cells from non-microbial cells in said test aliquot;
   d) transferring said isolated microbial cells into a culture medium suitable for microbial cell growth thereby to prepare a microbial culture preparation;
   e) inoculating a series of test microbial cultures for an antibiotic susceptibility test (AST) using the microbial culture preparation of step (d), wherein the series of test microbial cultures comprises at least two different growth conditions, wherein the different growth conditions comprise one or more different antimicrobial agents, and each antimicrobial agent is tested at two or more different concentrations;
   f) assessing the degree of microbial growth in each growth condition;
   wherein the concentration of microbial cells in said microbial culture preparation is determined between steps (d) and (e) and/or the concentration of microbial cells is determined in the test microbial cultures during or after step (e) but prior to step (f), and optionally and if necessary the concentration of microbial cells in said microbial culture preparation and/or said test microbial cultures is adjusted to a desired or pre-determined concentration; and
   wherein the degree of microbial growth in each growth condition is used to determine at least one MIC value for at least one antimicrobial agent, thereby to determine the antimicrobial susceptibility of said microorganism in said clinical sample.

2. The method of claim 1, wherein said clinical sample is blood or a blood fraction.

3. The method of claim 1, wherein said clinical sample culture is a primary culture of a clinical sample in a culture vessel containing culture medium.

4. The method of claim 1, wherein said clinical sample culture contains microbial cells derived from a separate clinical sample.

5. The method of claim 1, wherein the concentration of microbial cells in the clinical sample culture is less than $10^8$ CFU/ml.

6. The method of claim 5 wherein the concentration of microbial cells in the clinical sample culture is less than $10^7$ CFU/ml.

7. The method of claim 1, wherein non-microbial cells in the test aliquot are selectively lysed to obtain a microbial suspension and microbial cells are recovered from the microbial suspension.

8. The method of claim 7, wherein the microbial cells are recovered from said microbial suspension by filtration.

9. The method of claim 1, wherein the concentration of cells in the microbial culture preparation is adjusted to increase the number of cells by culturing the microbial culture preparation before step (e).

10. The method of claim 9, wherein the concentration of microbial cells in the microbial culture preparation is increased to a standard concentration of 0.5 McFarland units.

11. The method of claim 1, wherein the concentration of microbial cells in the microbial culture preparation is reduced by dilution before step (e).

12. The method of claim 11, wherein the concentration of microbial cells in the microbial culture preparation is reduced to a standard concentration.

13. The method of claim 7, wherein the concentration of microbial cells in the microbial culture preparation is determined again after or during the adjustment step.

14. The method of claim 1, wherein the concentration of microbial cells in the microbial culture preparation that is used to inoculate the series of test cultures in step (e) is not a standard concentration for AST, wherein the standard concentration is 0.5 McFarland units.

15. The method of claim 14, wherein the at least one MIC value obtained is adjusted based on the concentration of microbial cells in said culture to obtain a standard MIC value, wherein the standard MIC value is the MIC value of a microbial culture in which the concentration of microbial cells in the microbial culture is the standard concentration.

16. The method of claim 1, wherein the concentration of microbial cells in the test microbial culture is measured prior to step (f).

17. The method of claim 15, wherein the concentration of microbial cells in the test microbial culture is not the standard concentration for AST and wherein the at least one MIC value obtained is adjusted based on the concentration of microbial cells in said culture to obtain the standard MIC value.

18. The method of claim 1, wherein the assessing of the degree of microbial growth in step (f) is performed by determining the amount of microbial cell matter present in a test microbial culture.

19. The method of claim 18, wherein the determining of the amount of microbial cell matter includes determining at least one of:

the amount of at least one of (a) microorganisms and (b) microbial colonies or aggregates of microorganisms;

the number of at least one of (a) microorganisms and (b) microbial colonies or aggregates of microorganisms;

the size of microbial colonies or aggregates of microorganisms.

20. The method of claim 18, wherein the determining of the amount of microbial cell matter present is performed by imaging.

21. The method of claim 20, wherein the determining of the amount of microbial cell matter present is performed by measuring the area of microbial biomass by the imaging.

22. The method of claim 20, wherein the imaging is bright field imaging.

23. The method of claim 20, further comprising fluorescently labeling the microbial cells prior to step (f) and wherein the assessing of the degree of microbial growth in step (f) includes determining the degree of microbial growth by fluorescence microscopy.

24. The method of claim 1 wherein said clinical sample is from a subject having, or suspected of having, sepsis or septic shock.

25. The method of claim 1 wherein the culture vessel is a blood culture flask.

26. The method of claim 23, further comprising filtering the test aliquot to remove resin particles prior to step (c), wherein said filter comprises a pore size of at least 100 µm.

27. The method of claim 1, wherein the identity of the microorganism in the clinical sample is determined before step (b).

\* \* \* \* \*